(12) United States Patent
Greiner et al.

(10) Patent No.: US 12,179,022 B2
(45) Date of Patent: *Dec. 31, 2024

(54) METHODS AND SYSTEMS FOR TREATING OSTEOARTHRITIS USING AN IMPLANTABLE STIMULATOR

(71) Applicant: Valencia Bioscience, Inc., Valencia, CA (US)

(72) Inventors: Jeffrey H. Greiner, Valencia, CA (US); David K. L. Peterson, Valencia, CA (US); Stacy Greiner Chambliss, Valencia, CA (US)

(73) Assignee: Valencia Bioscience, Inc., Valencia, CA (US)

( * ) Notice: Subject to any disclaimer, the term of this patent is extended or adjusted under 35 U.S.C. 154(b) by 288 days.

This patent is subject to a terminal disclaimer.

(21) Appl. No.: 17/743,093

(22) Filed: May 12, 2022

(65) Prior Publication Data

US 2022/0266021 A1 Aug. 25, 2022

Related U.S. Application Data

(63) Continuation of application No. 16/667,346, filed on Oct. 29, 2019, now Pat. No. 11,357,984, which is a continuation of application No. 15/690,804, filed on Aug. 30, 2017, now Pat. No. 10,485,975.

(60) Provisional application No. 62/382,224, filed on Aug. 31, 2016.

(51) Int. Cl.
| | | |
|---|---|---|
| *A61N 1/36* | (2006.01) | |
| *A61H 39/00* | (2006.01) | |
| *A61N 1/372* | (2006.01) | |
| *A61N 1/05* | (2006.01) | |
| *A61N 1/375* | (2006.01) | |
| *A61N 1/378* | (2006.01) | |

(52) U.S. Cl.
CPC ....... *A61N 1/36071* (2013.01); *A61H 39/002* (2013.01); *A61N 1/36175* (2013.01); *A61N 1/36192* (2013.01); *A61N 1/36196* (2013.01); *A61N 1/37235* (2013.01); *A61N 1/0504* (2013.01); *A61N 1/0551* (2013.01); *A61N 1/36125* (2013.01); *A61N 1/3756* (2013.01); *A61N 1/378* (2013.01)

(58) Field of Classification Search
CPC ............ A61N 1/36071; A61N 1/36175; A61N 1/36192; A61N 1/36196; A61N 1/37235; A61N 1/378; A61H 39/002
See application file for complete search history.

(56) References Cited

U.S. PATENT DOCUMENTS

| | | | |
|---|---|---|---|
| 7,610,100 B2 | 10/2009 | Jaax et al. | |
| 10,485,976 B2* | 11/2019 | Streeter | A61N 1/36114 |
| 11,357,984 B2* | 6/2022 | Greiner | A61N 1/36175 |
| 2014/0214125 A1 | 7/2014 | Greiner et al. | |

* cited by examiner

*Primary Examiner* — Joseph M Dietrich
(74) *Attorney, Agent, or Firm* — ALG Intellectual Property, LLC

(57) ABSTRACT

A method of treating osteoarthritis includes an implantable stimulator generating stimulation sessions at a duty cycle that is less than 0.05 and applying the stimulation sessions by way of the central electrode and the annular electrode to a location within a patient that includes at least one of an acupoint labeled ST35, an acupoint labeled EX-LE-4, or a location on a line that intersects the acupoints labeled ST35 and EX-LE-4.

20 Claims, 24 Drawing Sheets

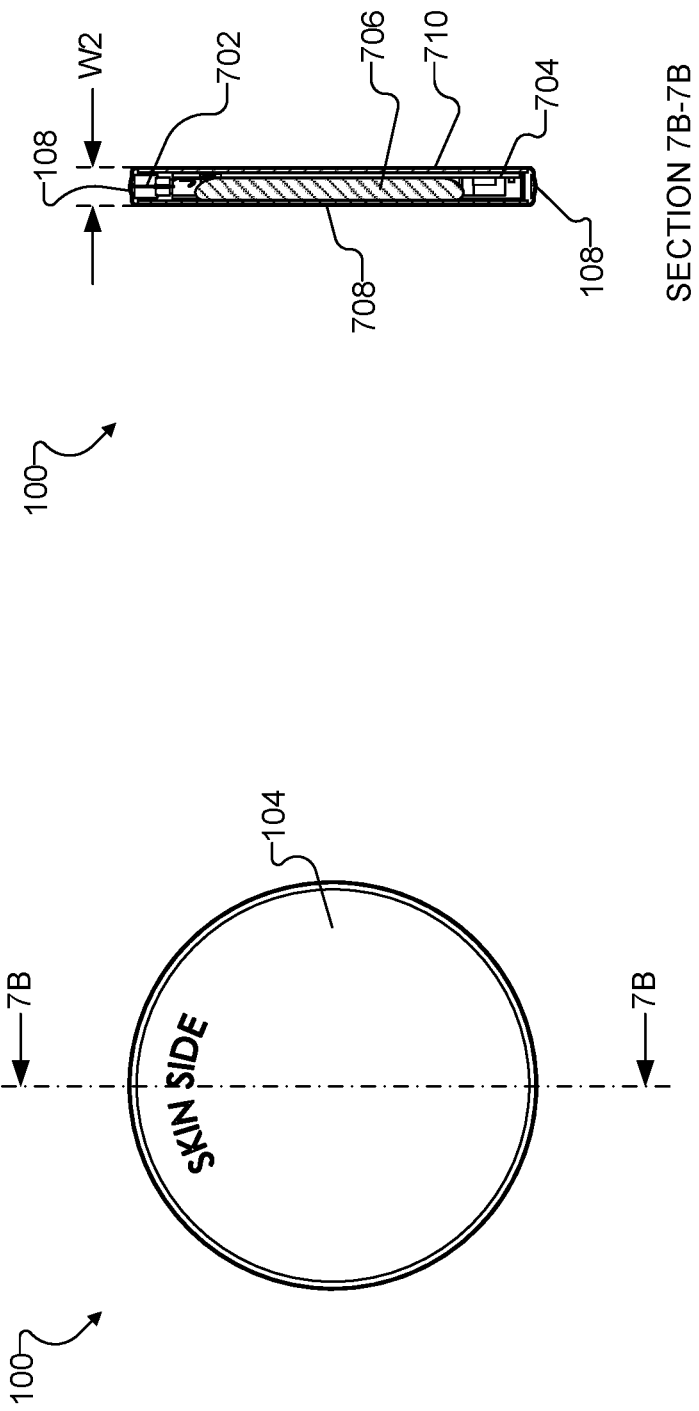

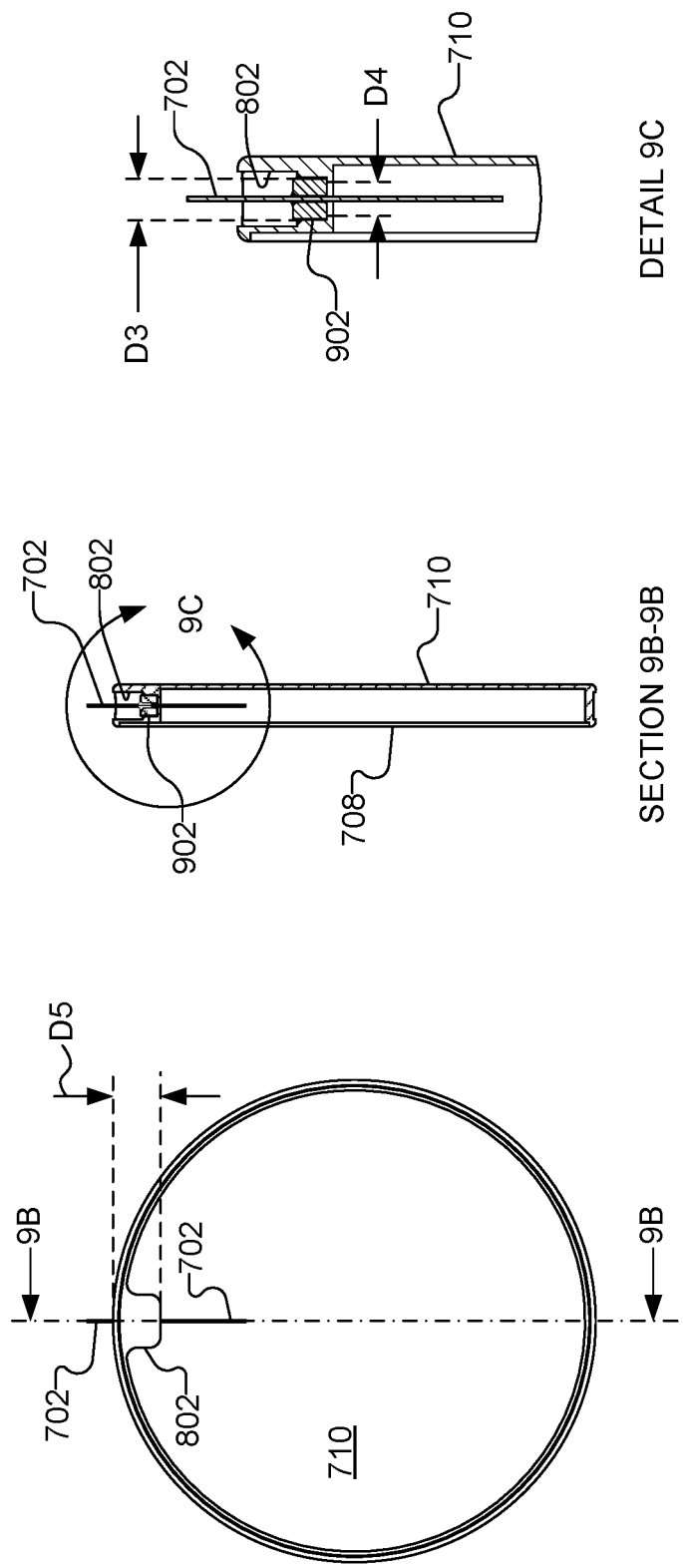

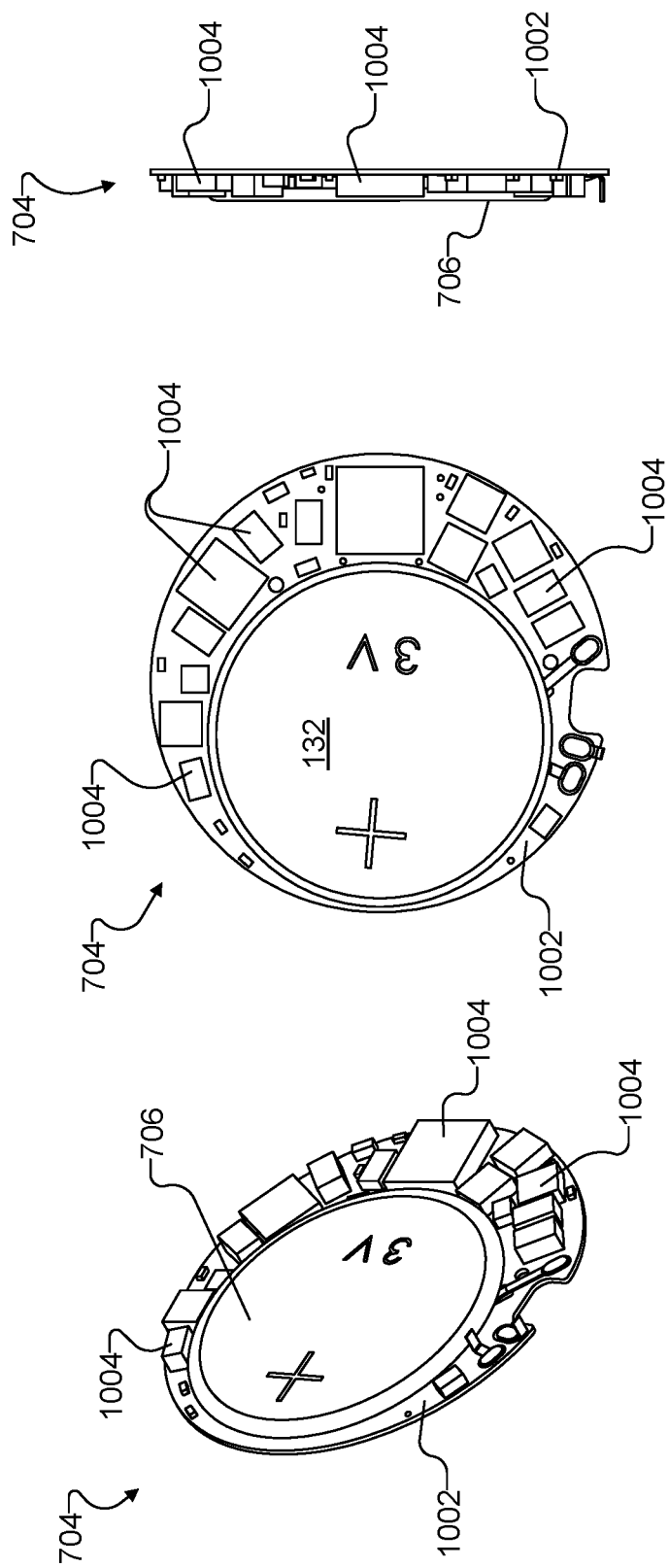

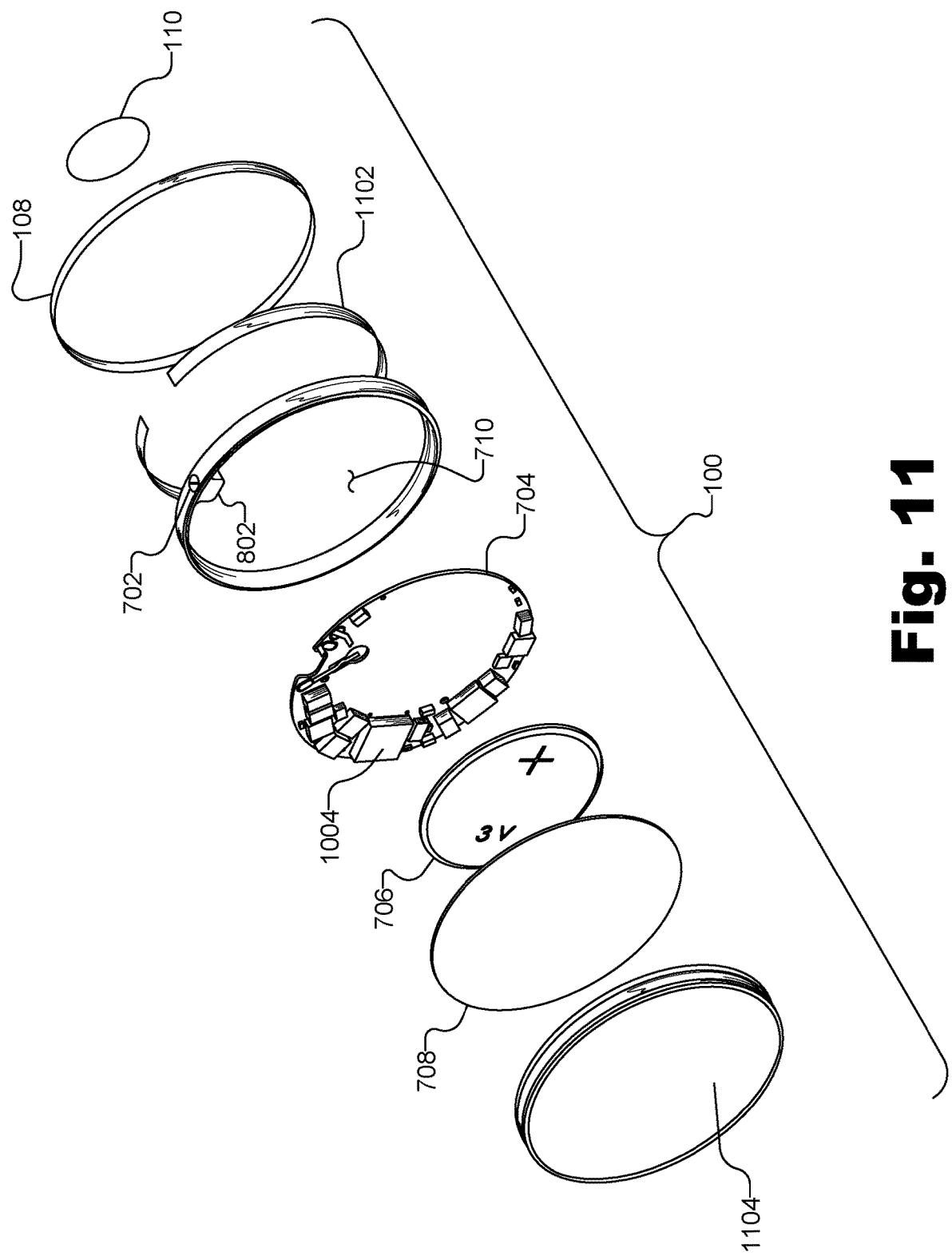

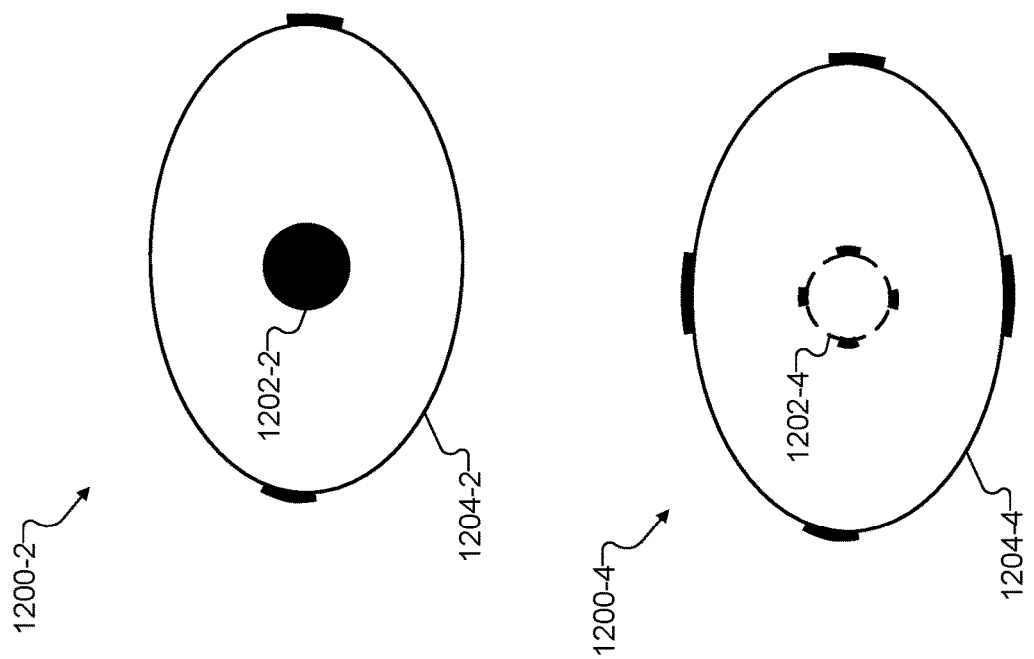
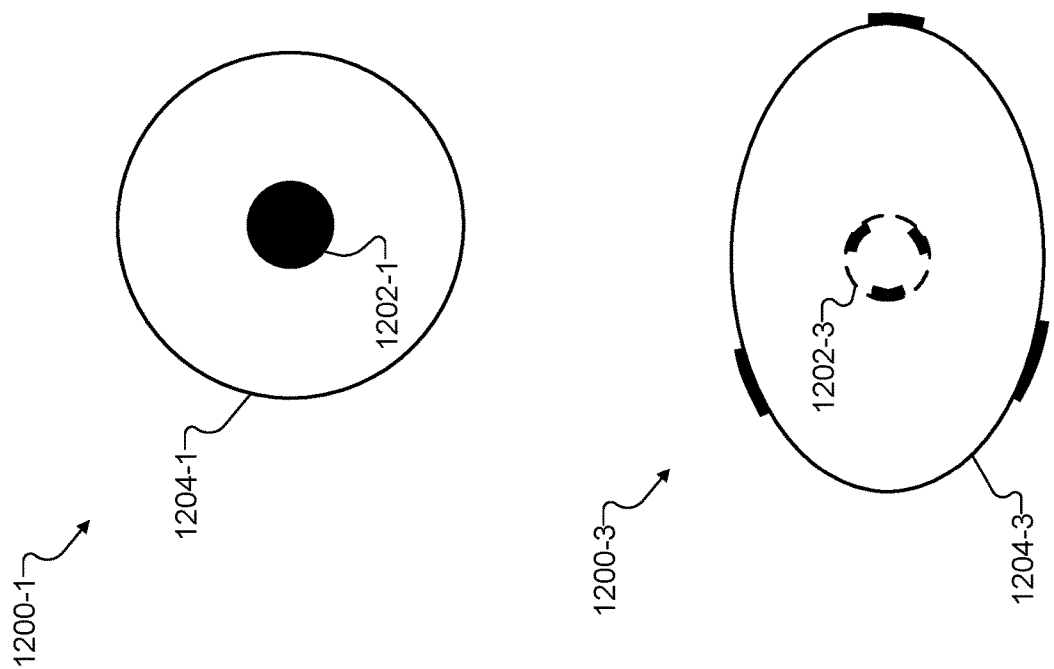
Fig. 12

METHODS AND SYSTEMS FOR TREATING OSTEOARTHRITIS USING AN IMPLANTABLE STIMULATOR

RELATED APPLICATIONS

The present application is a continuation application of U.S. patent application Ser. No. 16/667,346, filed Oct. 29, 2019, which is a continuation application of U.S. patent application Ser. No. 15/690,804, filed Aug. 30, 2017, now U.S. Pat. No. 10,485,975, which claims priority under 35 U.S.C. § 119(e) to U.S. Provisional Patent Application No. 62/382,224, filed Aug. 31, 2016, each of which is incorporated herein by reference in their respective entirety.

BACKGROUND INFORMATION

Osteoarthritis is a type of joint disease that results from breakdown of joint cartilage and underlying bone. Osteoarthritis commonly affects knees, hips, shoulders, and other joints, and often causes pain, decreased range of motion, and joint stiffness.

Unfortunately, it is often difficult to successfully treat osteoarthritis. Lifestyle modification (e.g., weight loss and exercise), medication, and surgery (e.g., joint replacement surgery) may alleviate some symptoms of osteoarthritis, but each of these treatment regimens has its drawbacks and risks.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

FIG. 7A illustrates an exemplary plan view of the other side of the housing of the EA device illustrated in FIG. 1 according to principles described herein.

FIG. 7B illustrates an exemplary sectional view of the EA device illustrated in FIG. 1 according to principles described herein.

FIG. 9A illustrates an exemplary plan view of the empty housing of the EA device illustrated in FIG. 8A according to principles described herein.

FIG. 9B illustrates an exemplary sectional view of the housing of the EA device illustrated FIG. 8A according to principles described herein.

FIG. 9C illustrates an enlarged view of a portion of FIG. 9B according to principles described herein.

FIG. 10A illustrates an exemplary perspective view of an electronic assembly adapted to fit inside of the empty housing of FIG. 8A and FIG. 8B according to principles described herein.

FIG. 10B illustrates an exemplary plan view of the electronic assembly shown in FIG. 10A according to principles described herein.

FIG. 10C illustrates an exemplary side view of the electronic assembly shown in FIG. 10A according to principles described herein.

FIG. 11 illustrates an exemplary exploded view of the EA device illustrated in FIG. 1, showing various constituent parts of the EA device according to principles described herein.

FIG. 12 illustrates exemplary alternative electrode configurations for the EA device illustrated in FIG. 1 according to principles described herein.

DETAILED DESCRIPTION

Methods and systems for treating osteoarthritis in a patient using an implantable electroacupuncture device are described herein. As will be described in more detail below, an electroacupuncture device implanted beneath a skin surface of the patient at a location (also referred to herein as an "acupoint") corresponding to a joint of the patient may generate stimulation sessions at a duty cycle that is less than 0.05 and apply the stimulation sessions to the joint. Each stimulation session may include a series of stimulation pulses, may have a duration of T3 minutes, and may occur at a rate of once every T4 minutes. As will be described below, the duty cycle may be defined to be a ratio of T3 to T4. The electroacupuncture device may include a central electrode of a first polarity centrally located on a surface of a housing of the electroacupuncture device and an annular electrode of a second polarity and that is spaced apart from the central electrode. In this configuration, the electroacupuncture device may apply the stimulation sessions to the joint by way of the central electrode and the annular electrode in accordance with the duty cycle. Additionally or alternatively, the electroacupuncture device may be powered by a coin-cell battery that has a thickness that is less than or equal to 3 millimeters ("mm").

Figure 1:
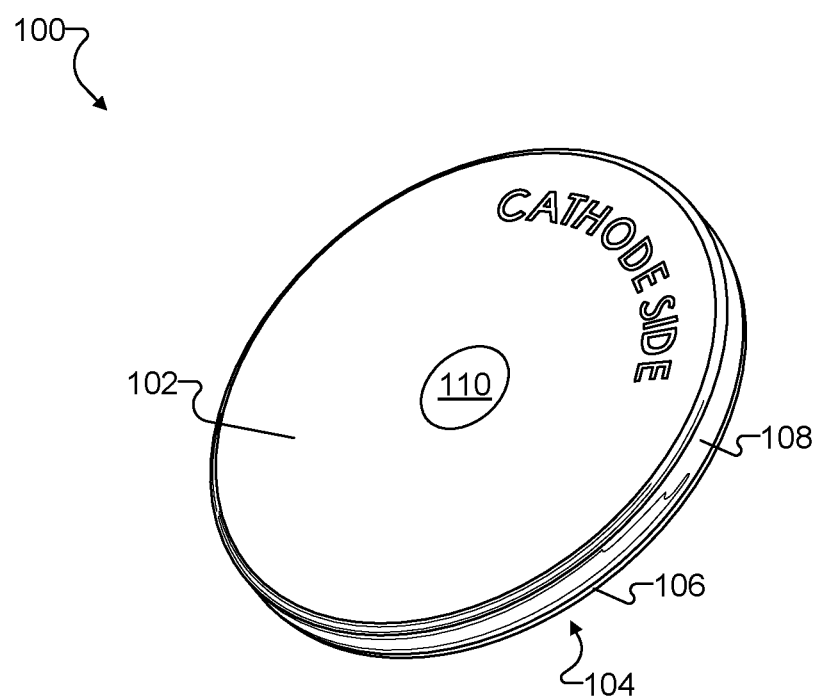
FIG. 1 illustrates a perspective view of an exemplary implantable electroacupuncture ("EA") device according to principles described herein.

FIG. 1 illustrates a perspective view of an exemplary leadless implantable electroacupuncture ("EA") device 100 configured to be implanted subcutaneously within a patient and used to perform neuromodulation therapy as a treatment for osteoarthritis. For example, EA device 100 may be configured to treat osteoarthritis through the application of stimulation sessions (where each stimulation session comprises a series of stimulation pulses) at a specified location (e.g., a specified acupoint) of a patient near an implantation site of EA device 100. As shown, EA device 100 may have the appearance of a disc or coin (e.g., having a diameter of approximately 23 mm, and a thickness of approximately 2 to 3 mm), and may include a bottom side 102, a top side 104, and an edge 106. In order to function properly, EA device 100 may include various components located (e.g., hermetically sealed) within a housing of EA device 100 provided by bottom side 102, top side 104, and edge 106. For example, EA device 100 may include pulse generation circuitry configured to deliver stimulation sessions to the patient's body tissue at the specified acupoint, a primary (i.e., not rechargeable) battery configured to provide operating power for EA device 100 to function, a communication subsystem (e.g., a coil and/or a sensor) for receiving and responding to operating commands wirelessly communicated to EA device 100 from a non-implanted location to externally control EA device 100 (e.g., to turn EA device 100 ON or OFF, to adjust an amplitude of stimulation sessions produced by EA device 100, etc.), and/or any other components that may serve a particular implementation.

To generate a stimulation session, EA device 100 may include an annular electrode 108 placed around a perimeter of edge 106, and a central electrode 110 centrally located on bottom side 102, as shown in FIG. 1. Annular electrode 108 may serve as an anode electrode and central electrode 110 may serve as a cathode electrode, or vice versa. Additionally, an insulating later (not explicitly shown) may be included around edge 106 between edge 106 and annular electrode 108, and a layer of silicone molding (not explicitly shown) may cover some or all of the housing of EA device 100 (e.g., bottom side 102, top side 104, and edge 106). For example, silicone molding may be used to insulate the entire housing of EA device 100, leaving only annular electrode 108 and central electrode 110 exposed in order to better control electric fields established between annular electrode 108 and central electrode 110 and to prevent the entire housing of EA device 100 from acting as a cathode electrode.

In operation, EA device 100 may be implanted below the skin surface of the patient at a location that corresponds to the joint affected by osteoarthritis. For example, if the patient is suffering from osteoarthritis of the knee, EA device 100 may be implanted at a location that corresponds to the knee (e.g., an acupoint labeled ST35, an acupoint labeled LE4, and/or a location on a line that intersects the acupoints labeled ST35 and LE4). As another example, if the patient is suffering from osteoarthritis of the shoulder, EA device 100 may be implanted at a location that corresponds to the shoulder (e.g., an acupoint labeled TB14, an acupoint labeled LI15, an acupoint labeled SI10, and/or a location associated with an axillary nerve of the patient). As another example, if the patient is suffering from osteoarthritis of the hip, EA device 100 may be implanted at a location that corresponds to the hip (e.g., an acupoint labeled GB29, an acupoint labeled GB30, an acupoint labeled GB34, and/or a location associated with a sciatic nerve of the patient).

In some examples, EA device 100 may generate stimulation sessions in accordance with a specified stimulation regimen. For example, the stimulation regimen may prescribe that a relatively short series of stimulation pulses be applied to the specified acupoint during a short session (e.g., a thirty-minute session) that is separated by a relatively long period of time (e.g., seven days) from other stimulation sessions. As such, a duty cycle of the stimulation sessions may be very low (e.g., less than 0.05). Additionally, a duty cycle of the stimulation pulses applied during a stimulation may also be very low.

As shown, one advantage of EA device 100 may be a simple, leadless design. Specifically, electrodes 108 and 110 may be directly attached to the housing of EA device 100 rather than to leads configured to be positioned and anchored at desired stimulation sites away from the location that EA device 100 is implanted. As a result, implanting EA device 100 within a patient may be less invasive and/or less risky to the patient than implant procedures for implants having leads that must be tunneled through body tissue or blood vessels to reach desired stimulation sites. In other implementations, other types of implantable stimulators (e.g., implantable stimulators with leads connected thereto) may also be used in accordance with the methods and systems described herein. For example, application of stimulation sessions to an affected joint may be performed by applying the stimulation sessions by way of an electrode included on a lead connected to EA device 100.

Figure 2:
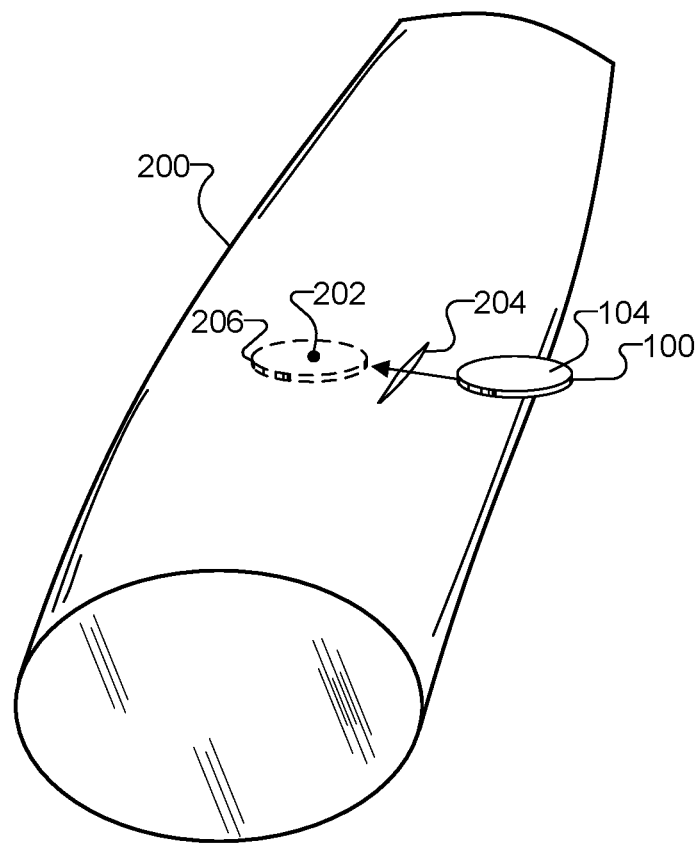
FIG. 2 illustrates a view of a limb of a patient where a specified acupoint has been identified and selected, and illustrates a manner of implanting the EA device illustrated in FIG. 1 at the selected acupoint according to principles described herein.

FIG. 2 shows a view of a limb 200 of a patient. A specified acupoint 202 known to moderate or affect osteoarthritis in a joint of a patient may have been identified and selected in limb 200 to receive electroacupuncture treatment. Accordingly, FIG. 2 illustrates a manner of implanting EA device 100 at acupoint 202 to provide the electroacupuncture treatment to the joint. In particular, an incision 204 may be made into limb 200 near (e.g., 10 to 15 mm away from) acupoint 202. A slot may be formed at incision 204 (e.g., by lifting up the skin closest to acupoint 202) and a pocket 206 may thus be formed under the skin at the location of acupoint 202 to receive EA device 100. Subsequently, with top side 104 facing up (i.e., facing the skin), EA device 100 may be slid through the slot of incision 204 and into pocket 206 so that EA device 100 is centered at specified acupoint 202. Then, with EA device 100 in place, incision 204 may be sewn up or otherwise closed and EA device 100 may be left under the patient's skin at the acupoint 202 location so that subcutaneous neuromodulation therapy may be performed by applying the stimulation sessions as described above. Advantageously, the implantation surgery of EA device 100 may often be completed in less than ten minutes in an outpatient setting or in a doctor's office. Only minor, local anesthesia may be used and no significant risks may be associated with the implant procedure. Also, if desired, EA device 100 may be quickly explanted in a similarly safe and easy surgical procedure.

Figure 3:
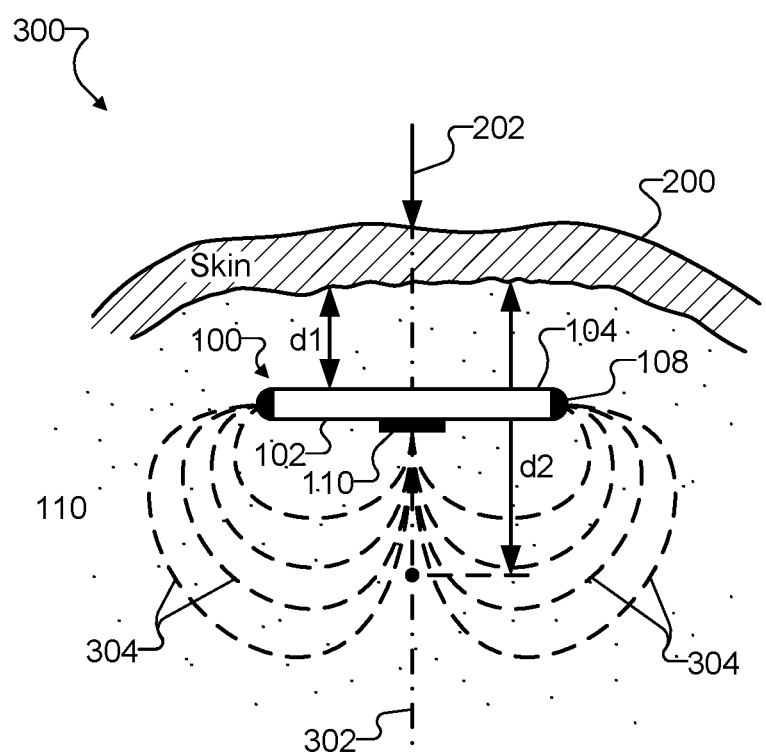
FIG. 3 illustrates a cross-sectional view of the EA device illustrated in FIG. 1 implanted at a selected acupoint within a patient according to principles described herein.

FIG. 3 illustrates a cross-sectional view 300 of EA device 100 implanted at acupoint 202 within limb 200 of the patient. As shown, EA device 100 may be implanted at a depth d1 under the skin (e.g., approximately 2 mm to 4 mm under the skin). Top side 104 of EA device 100 may be facing up to the skin of the patient, while bottom side 102 of EA device 100, upon which central electrode 110 is disposed, may be facing down away from the skin. As illustrated by cross-sectional view 300, EA device 100 may provide a symmetrical electrode configuration where central electrode 110 is centrally located on an acupoint axis 302 extending orthogonally into the skin from a location on the skin where acupoint 202 is indicated, and where annular electrode 108, which may be implemented as a ring electrode, encircles central electrode 110 and acupoint axis 302.

The symmetry between central electrode 110 at the center and annular electrode 108 encircling central electrode 110 may help focus an electric field generated by electrodes 110 and 108, promoting stimulation current generated by application of a stimulation pulse to flow into tissue below the central electrode, where it may be desired that electroacupuncture stimulation should be applied. For example, while acupoint 202 is illustrated in FIGS. 2 and 3 as being on the surface of the skin, electroacupuncture treatment may be most effective at a distance d2 below the skin surface along acupoint axis 302. The ideal distance d2 may vary depending upon where the acupoint is located on the body and/or depending on an aim of the acupuncture treatment to be performed.

Also illustrated in view 300 are electric field gradient lines 304, which may be created by an electroacupuncture pulse applied to tissue within the patient by annular electrode 108 and/or central electrode 110. As shown, electric field gradient lines 304 are strongest along a line coinciding with, or near to, acupoint axis 302. Accordingly, FIG. 3 illustrates that one of the primary advantages of the symmetrical electrode configuration of EA device 100 is that the precise orientation of EA device 100 within the patient is not important. Rather, as long as EA device 100 is centered at acupoint 202 (i.e., such that acupoint axis 302 passes through the center of EA device 100) and central electrode 110 is facing down, a strong electric field (e.g., illustrated by electric field gradient lines 304) may be generated to align with acupoint axis 302. As a result, EA stimulation current may flow along (or very near) acupoint axis 302, and the desired electroacupuncture stimulation may properly be applied to the tissue at a depth d2 below the acupoint 202 location indicated on the skin.

Figure 4A:
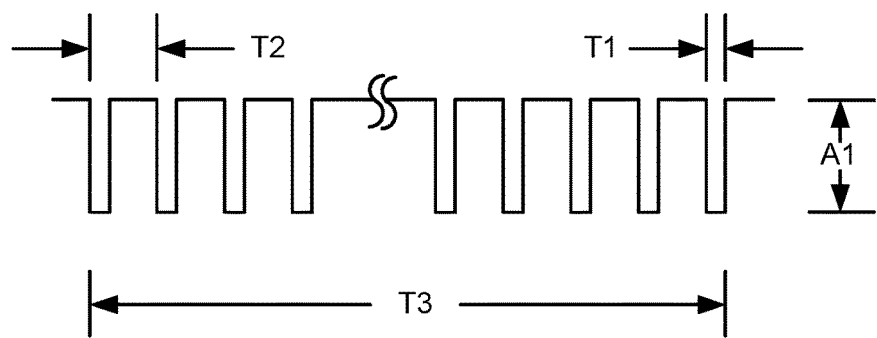
FIGS. 4A and 4B illustrate exemplary timing waveform diagrams showing exemplary stimulation parameters used by the EA device illustrated in FIG. 1 to generate stimulation pulses according to principles described herein.
Figure 4B:
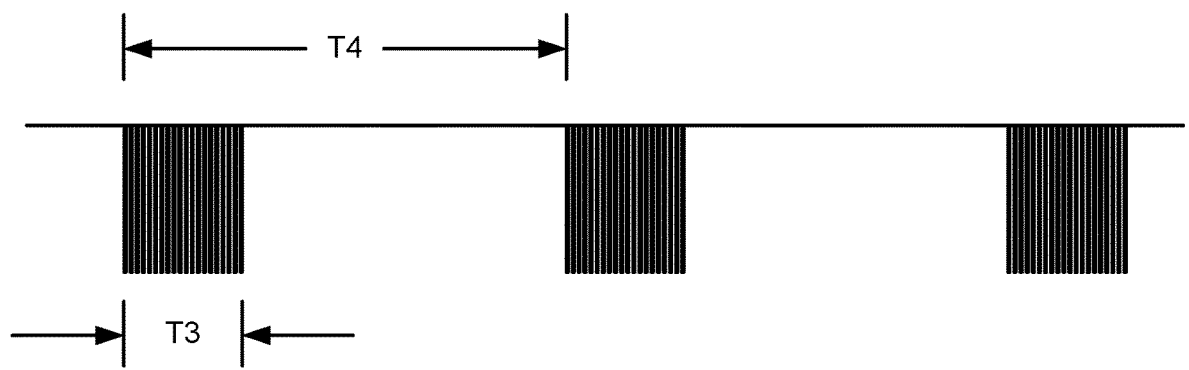

FIGS. 4A and 4B show timing waveform diagrams illustrating exemplary EA stimulation parameters used by the EA device to generate stimulation pulses. As seen in FIG. 4A, four stimulation parameters may be associated with a stimulation session. The time T1 defines the duration (or pulse width) of a stimulus pulse. The time T2 defines the time between the start of one stimulus pulse and the start of the next stimulus pulse. The time T2 thus defines the period associated with the frequency of the stimulus pulses. The frequency of the stimulation pulses is equal to 1/T2. The ratio of T/T2 is typically quite low, e.g., less than 0.01, but may, in some instances, be as much as 0.03. The duration of a stimulation session is dictated or defined by the time period T3, and may be, for example, at least 10 minutes and less than 60 minutes (e.g., 30-40 minutes). The amplitude of the stimulation pulses is defined by the amplitude A1. This amplitude may be expressed in either voltage or current.

In some examples, in order to effectively treat osteoarthritis, the stimulation pulses may be applied to the joint at a frequency that is less than or equal to 10 Hz (e.g., 2 Hz). Additionally or alternatively, the stimulation pulses may be alternatingly applied to the joint at a frequency that is less than or equal to 10 Hz (e.g., 2 Hz) and a frequency that is greater than or equal to 50 Hz (e.g., 100 Hz). Both of these stimulation frequency regimens have been shown to be effective in treating osteoarthritis.

FIG. 4B illustrates the manner in which the stimulation sessions are administered in accordance with a specified stimulation regimen. FIG. 4B shows several stimulation sessions of duration T3, and how often the stimulation sessions occur. The stimulation regimen thus includes a time period T4 which sets the time period from the start of one stimulation session to the start of the next stimulation session and may be, for example, at least 1440 minutes (and, in some examples, less than 10*1440=14,400 minutes). T4 thus is the period of the stimulation session frequency, and the stimulation session frequency is equal to 1/T4.

In order to allow the applied stimulation to achieve its desired effect on the body tissue at the selected target stimulation site, the period of the stimulation session T4 may be varied when the stimulation sessions are first applied. This can be achieved by employing a simple algorithm within the circuitry of the EA device that changes the value of T4 in an appropriate manner. For example, at start up, the period T4 may be set to a minimum value, T4 (min). Then, as time goes on, the value of T4 may be gradually increased until a desired value of T4, T4 (final), is reached.

By way of example, if T4 (min) is 1 day, and T4 (final) is 7 days, the value of T4 may vary as follows once the stimulation sessions begin: T4=1 day for the duration between the first and second stimulation sessions, then 2 days for the duration between the second and third stimulation sessions, then 4 days for the duration between the third and fourth stimulation sessions, and then finally 7 days for the duration between all subsequent stimulation sessions after the fourth stimulation session.

Rather than increasing the value of T4 from a minimum value to a maximum value using a simple doubling algorithm, as described in the previous paragraph, an enhancement is to use a table that defines session durations and intervals whereby the automatic session interval can be shorter for the first week or so. For example, if T3 is 30 minutes, the first 30-minute session may be delivered after 1 day, the second 30-minute session may be delivered after 2 days, the third 30-minute session may be delivered after 4 days, and the fourth 30-minute session may be delivered for all subsequent sessions after 7 days. If a triggered session is delivered completely, it advances the therapy schedule to the next table entry.

By way of example, one exemplary set of parameters that could be used to define a stimulation regimen is as follows:
T1=0.5 milliseconds
T2=500 milliseconds
T3=30 minutes
T4=7 days (10,080 minutes)
A1=15 volts (across 1 KΩ), or 15 milliamps (mA)

An example of typical ranges for each parameter, for treating osteoarthritis, is as follows:
T1=0.1 to 2.0 milliseconds (ms)
T2=67 to 1000 ms (15 Hz to 1 Hz)
T3=20 to 60 minutes
T4=1,440 to 10,080 minutes (1 day to 1 week)
A1=1 to 15 mA The values shown above for the stimulation regimen and ranges of stimulation parameters for use within the stimulation regimen are only exemplary. In some examples, the ratio of T3 to T4, which defines the duty cycle, may be specifically configured to treat osteoarthritis. For example, EA device 100 may receive a control command from a device external to EA device 100 that sets the times T3 and T4 to appropriate values configured to treat osteoarthritis. As such, EA device 100 may perform the stimulation sessions in accordance with the received control command. The external device may communicate the control command in any way as may serve a particular implementation. For example, receiving the control command may include detecting, with a magnetic field sensor included in EA device 100, a magnetic field generated by the device external to EA device 100. Techniques whereby the magnetic field sensor may detect the control command will be described in more detail below.

In some examples, the ratio of T3 to T4 may be specified (e.g., by the control command) to be very low (e.g., no more than 0.05). Maintaining a low duty cycle of this magnitude may represent a significant change over prior implantable stimulators. For example, by using a very low duty cycle, a small battery (e.g., a coin-sized cell) with a relatively high internal impedance (e.g., at least 5 ohms) may be used to provide power to EA device 100 for a long period of time (e.g., several years). One benefit of such a small battery, in turn, is that the housing of EA device 100 may be compact and small, allowing EA device 100 to be implanted and used with or without leads. As such, EA device 100 may be relatively easy to implant at the desired stimulation site (e.g., acupoint) as long as the frequency and duration of stimulation sessions are limited.

Limiting the frequency and duration of the stimulation sessions may be beneficial because doing so may account for the fact that some treatments are best done slowly and methodically, over time, rather than quickly and harshly using large doses of stimulation (or other treatments) aimed at forcing a rapid change in the condition of the patient. In addition, a slow and methodical conditioning is consistent with the time scale for remodeling of the central nervous system needed to produce a sustained therapeutic effect.

Figure 5A:
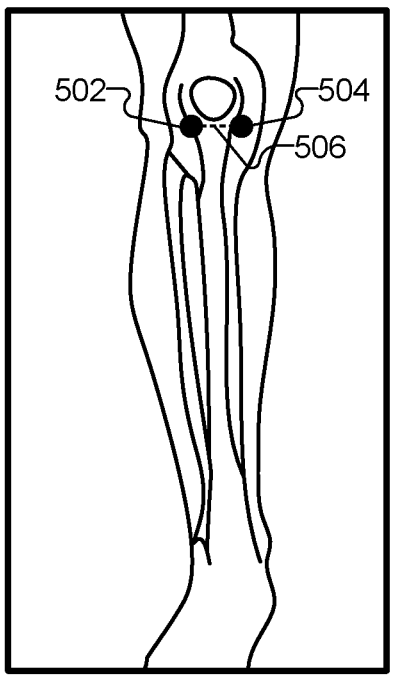
FIGS. 5A-5C illustrates exemplary acupoints according to principles described herein.
Figure 5B:
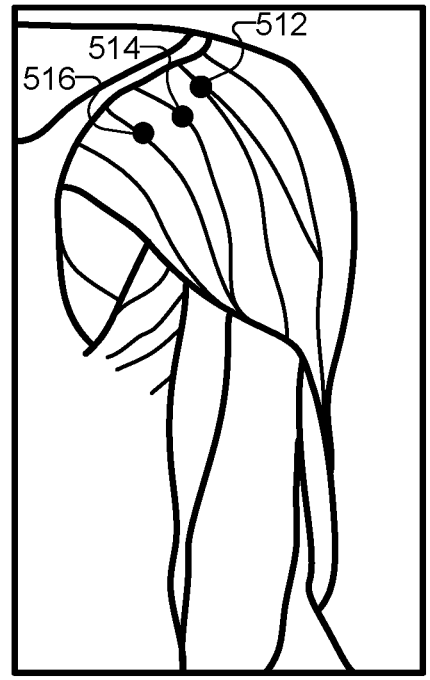
Figure 5C:
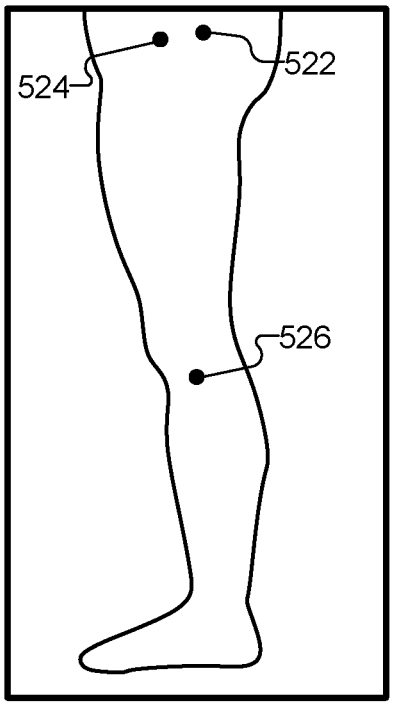

FIGS. 5A-5C illustrate various acupoints within the body at which EA device 100 may be placed and used to treat osteoarthritis. In particular, FIG. 5A illustrates various acupoints at which EA device 100 may be placed and used to treat osteoarthritis of the knee, FIG. 5B illustrates various acupoints at which EA device 100 may be placed and used to treat osteoarthritis of the shoulder, and FIG. 5C illustrates various acupoints at which EA device 100 may be placed and used to treat osteoarthritis of the hip. It will be recognized that the acupoints illustrated in FIGS. 5A-5C are merely illustrative, and that EA device 100 may be placed at any suitable location within the patient as may serve a particular implementation. It will also be recognized that will the knee, shoulder, and hip are shown as specific examples of joints that may be affected by osteoarthritis, it will be recognized that the methods and systems described herein may be used to treat osteoarthritis in any other joint as may serve a particular implementation.

FIG. 5A shows that an acupoint 502 labeled ST35 and an acupoint labeled LE4 (also referred to as "EX-LE-4") are located within a vicinity of the knee. These two acupoints are referred to as "eyes of the knee". In some examples, EA device 100 (or an electrode lead, such as a pigtail leadwire, connected to EA device 100) may be placed at acupoint 502 and/or acupoint 504 in order to effectively treat osteoarthritis of the knee. Alternatively, EA device 100 (or an electrode lead connected to EA device 100) may be placed anywhere along a line 506 that intersects both acupoints 502 and 504.

FIG. 5B shows various acupoints 512, 514, and 516 that are associated with the shoulder. Acupoint 512 may be referred to as TB14, acupoint 514 may be referred to as LI15, and acupoint 516 may be referred to as SI10. Stimulation of each of these acupoints may stimulate the axillary nerve, which may be effective in treating osteoarthritis of the shoulder. Hence, EA device 100 (or an electrode lead connected to EA device 100) may be placed at one of these acupoints, or at any other location associated with the axillary nerve, in order to effectively treat osteoarthritis of the shoulder.

FIG. 5C shows various acupoints 522, 524, and 526 that are associated with the hip. Acupoint 522 may be referred to as GB29, acupoint 524 may be referred to as GB30, and acupoint 526 may be referred to as GB34. Stimulation of each of these acupoints may stimulate the sciatic nerve, which may be effective in treating osteoarthritis of the hip. Hence, EA device 100 (or an electrode lead connected to EA device 100) may be placed at one of these acupoints, or at any other location associated with the sciatic nerve, in order to effectively treat osteoarthritis of the hip.

Various mechanical and electrical features of EA device 100 will now be described. These and additional features of EA device 100 are described in more detail in United States Patent Application Publication No. 2014/0214113, which is incorporated herein by reference in its entirety.

Figure 6B:
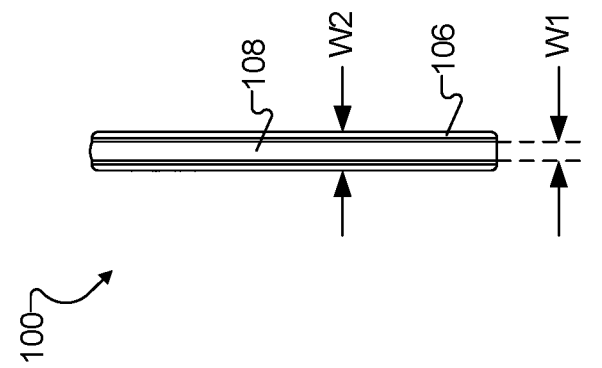
FIG. 6B illustrates an exemplary side view of the housing of the EA device illustrated in FIG. 1 according to principles described herein.
Figure 6A:
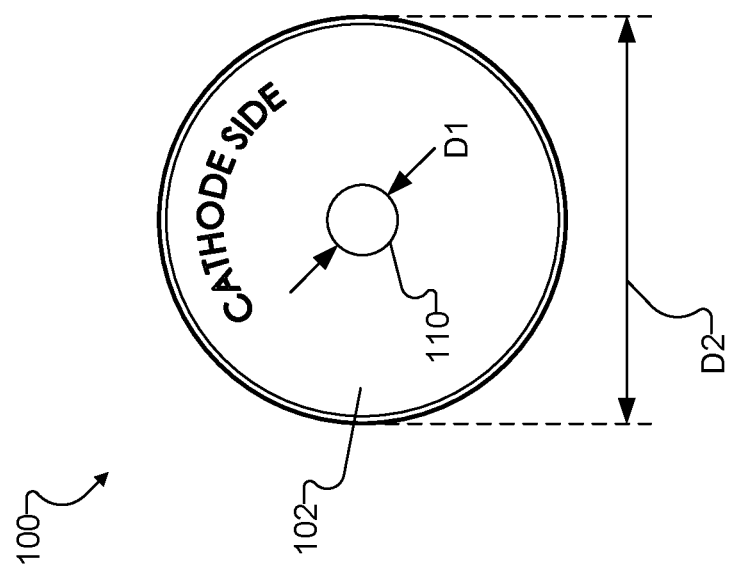
FIG. 6A illustrates an exemplary plan view of one surface of the housing of the EA device illustrated in FIG. 1 according to principles described herein.

FIG. 6A shows a plan view of bottom side 102 (i.e., the "cathode" or "front" side) of EA device 100, described above in relation to FIG. 1. As shown in FIG. 6A, cathode electrode 110 appears as a circular electrode, centered on the front side, having a diameter D1. As further shown in FIG. 6A, the housing of EA device 100 has a diameter D2. In various examples, D1 and D2 may be any suitable diameters as may serve a particular implementation. For example, D1 may be approximately 4 mm and D2 may be approximately 23 mm.

FIG. 6B shows a side view of EA device 100 illustrating edge 106 and annular electrode 108, as described above in relation to FIG. 1. As illustrated by FIG. 6B, the housing of EA device 100 may have an overall thickness of width W2, while annular electrode 108 may have a width W1. In various examples, W1 and W2 may be any suitable widths as may serve a particular implementation. For example, W1 may be approximately 1.0 mm, or approximately one half of width W2, which may be approximately 2.0 mm or slightly more than 2.0 mm (e.g., 2.2 mm).

FIG. 7A shows a plan view of top side 104 (i.e., the "back" or "skin" side) of EA device 100, described above in relation to FIG. 1. FIG. 7B shows a sectional view of EA device 100 taken along the line 7B-7B of FIG. 7A. Visible in this sectional view is a feed-through pin 702, including a distal end of feed-through pin 702 attached to annular electrode 108. Also visible in this sectional view is an electronic assembly 704 on which various electronic components are mounted, including a disc-shaped battery 706. FIG. 7B further illustrates that a cover plate 708 may be welded, or otherwise bonded, to a bottom case 710 in order to form the hermetically-sealed housing of EA device 100.

As will be described and illustrated in more detail below, top side 104 of EA device 100 comprises cover plate 708, which may be welded in place once bottom case 710 has all of the electronic circuitry and other components placed inside of the housing.

Figure 8A:
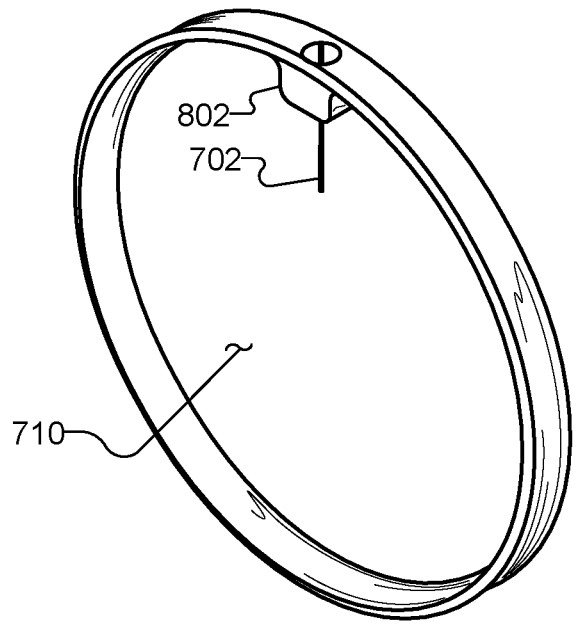
FIG. 8A illustrates an exemplary perspective view of the housing of the EA device illustrated in FIG. 1 before the electronic components are placed therein according to principles described herein.

FIG. 8A shows a perspective view of bottom case 710, including feed-through pin 702, before the electronic components are placed therein, and before being sealed with cover plate 708. Bottom case 710 is similar to a shallow "can" without a lid, having a short side wall around its perimeter. Alternatively, bottom case 710 may be viewed as a short cylinder, closed at one end but open at the other. (Note, in the medical device industry the housing of an implanted device may often be referred to as a "can".) As shown, feed-through pin 702 may pass through a segment of the side wall of bottom case 710 that is at the bottom of a recess cavity 802 formed in the wall. The use of recess cavity 802 to hold feed-through pin 702 may help keep temperature-sensitive portions of the feed-through assembly (e.g., portions that could be damaged by excessive heat) away from the thermal shock and residual weld stress inflicted upon bottom case 710 when the cover plate 708 is welded thereto.

Figure 8B:
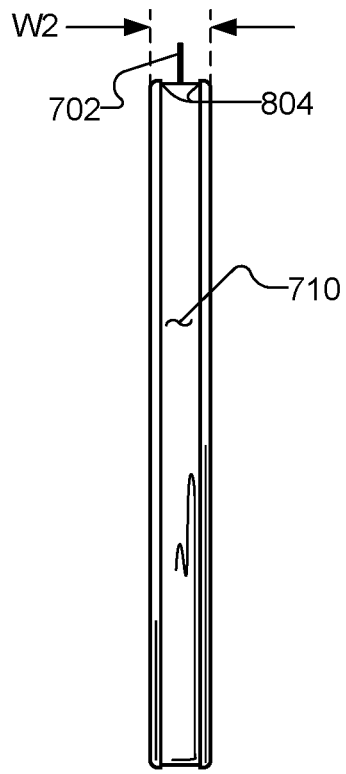
FIG. 8B illustrates an exemplary side view of the housing of the EA device illustrated in FIG. 1 according to principles described herein.

FIG. 8B is a side view of bottom case 710, and shows annular rims 804 formed on both sides of bottom case 710. Annular electrode 108 may fit between annular rims 804 when annular electrode 108 is positioned around the edge of bottom case 710. It will be understood that, in certain examples, annular electrode 108 is used as an anode electrode and, hence, may be referred to as a ring anode electrode. However, in other examples, annular electrode 108 may be employed as a cathode electrode. As will be illustrated and described in more detail below, a silicone insulator layer may be placed between the backside of annular electrode 108 and the perimeter edge of bottom case 710 where annular electrode 108 is placed around the edge of bottom case 710.

FIG. 9A shows a plan view of bottom case 710 shown in the perspective view of FIG. 8A. For example, in FIG. 9A, bottom case 710 is shown to be empty. Additionally, an outline of recess cavity 802 and feed-through pin 702 are also illustrated in FIG. 9A. As shown, a bottom edge of recess cavity 802 is located a distance D5 radially inward from the edge of bottom case 710. For example, in certain examples, distance D5 may be between approximately 2.0 to 2.5 mm. As shown in FIG. 9A, feed-through pin 702 (e.g., formed form a piece of solid wire) may extend radially outward from bottom case 710 above recess cavity 802 and radially inward from recess cavity 802 toward the center of bottom case 710. In certain examples, feed-through pin 702 may be trimmed (e.g., the length may be shortened as compared to the illustration of feed-through pin 702 in FIG. 9A) when a distal end that extends above recess cavity 802 is connected to annular electrode 108 (e.g., by passing through a hole in annular electrode 108 and being welded to annular electrode 108), and when a proximal end is connected to an output terminal of the electronic assembly 704 (not explicitly illustrated in FIG. 9A).

FIG. 9B depicts a sectional view of the housing of EA device 100 illustrated in FIG. 9A taken along the section line 9B-9B of FIG. 9A. Similarly, FIG. 9C shows an enlarged view depicting additional detail of the portion of FIG. 9B that is encircled with the line 9C. Together, FIGS. 9B and 9C illustrate that feed-through pin 702 may be embedded within an insulator 902, which may have a diameter of D3. The feed-through pin assembly (i.e., the combination of feed-through pin 702 and insulator 902, into which feed-through pin 702 is embedded) may reside on a shoulder around an opening or hole formed in the bottom of recess cavity 802 having a diameter D4. Diameters D3 and D4 may be any suitable diameters that may serve a particular implementation. For example, diameter D3 may be approximately 0.95 mm, with approximately a 0.07 mm tolerance, and diameter D4 may be approximately 0.80 mm, with approximately a 0.06 mm tolerance.

Components illustrated in FIGS. 9B and 9C may be made of any suitable materials that may serve a particular implementation. For example, feed-through pin 702 may be made of pure platinum 99.95%, insulator 902 may be made of ruby or alumina, and bottom case 710 and/or cover plate 708 may be made of titanium. Additionally, the feed-through assembly (e.g., feed-through pin 702 and insulator 902) and bottom case 710 may be hermetically sealed as a unit by gold brazing. In certain examples, another brazing (e.g., an active metal brazing allowing metal to be joined to ceramic without metallization) may be used.

To test the hermeticity of the sealed housing of EA device 100, a helium leak test commonly used in the medical device industry may be used. In some examples, the helium leak rate should not exceed $1 \times 10^{-9}$ STD cc/sec at 1 atm pressure if the housing of EA device 100 is properly sealed. Other tests may also be performed to verify the case-to-pin resistance (e.g., which should be at least $15 \times 10^6$ Ohms at 100 volts DC), the avoidance of dielectric breakdown or flashover between the pin and bottom case 710 (e.g., tested at 400 volts AC RMS at 60 Hz), and thermal shock characteristics.

One advantage provided by the feed-through assembly shown in FIGS. 8B, 9A, 9B and 9C is that the feed-through assembly (i.e., including feed-through pin 702, insulator 902, and recess cavity 802 formed from the material of bottom case 710) may be fabricated and assembled before any other components of EA device 100 are placed inside of bottom case 710. This advantage may significantly facilitate the manufacture of EA device 100.

FIG. 10A illustrates a perspective view of electronic assembly 704, described above in relation to FIG. 7. As shown, electronic assembly 704 may include a multi-layer printed circuit (PC) board 1002, or equivalent mounting structure, on which battery 706 and various electronic components 1004 may be mounted. This assembly is adapted to fit inside of the empty bottom case 710, described above in relation to FIGS. 8A-8B and FIGS. 9A-9C.

FIGS. 10B and 10C show a plan view and side view, respectively, of electronic assembly 704. As illustrated, electronic components 1004 may be assembled and connected together so as to perform proper circuit functions to allow EA device 100 to perform its intended functions. The circuit functions performed by electronic components 1004 (i.e., by electronic assembly 704) will be explained in more detail below.

FIG. 11 illustrates an exemplary exploded view of the entirety of EA device 100. As illustrated in FIG. 11, EA device 100 includes, starting from the right and moving toward the left, central electrode 110 (e.g., a cathode electrode), annular electrode 108 (e.g., an anode electrode), an insulating layer 1102, bottom case 710 (i.e., the "can" portion of the housing of EA device 100), electronic assembly 704 (e.g., including battery 706 and electronic components 1004 mounted on PC board 1002), cover plate 708, and a layer of silicon molding 1104.

While certain details may not be fully illustrated in FIG. 11, it will be understood that the components illustrated in FIG. 11 may be assembled in any way as may serve a particular implementation, including in any way described herein. For example, as described above, feed-through pin 702 may pass through an opening in the bottom of recess cavity 802 formed as part of bottom case 710, but feed-through pin 702 may be insulated (e.g., by insulator 902) so as to not make electrical contact with metal that may be included in bottom case 710. Additionally, cover plate 708 may be connected to bottom case 710 in any suitable way. For example, cover plate 708 may be welded to the edge of bottom case 710 (e.g., using laser beam welding or another equivalent process), as one of the final steps in the assembly process.

Additionally, other components not necessarily shown or identified in FIG. 11 may be included in the assembly of EA device 100. For example, EA device 100 may include adhesive patches for bonding battery 706 to PC board 1002 of electronic assembly 704, and/or for bonding electronic assembly 704 to the inside of bottom case 710. To prevent high temperature exposure of battery 706 during the assembly process, conductive epoxy may be used to connect a battery terminal to PC board 1002. Because the curing temperature of conductive epoxy may be relatively high (e.g., 125 degrees Celsius), the following process may be used. First, the conductive epoxy of a battery terminal ribbon may be cured to PC board 1002 without battery 706. Second, battery 706 may be glued to PC board 1002 using room temperature cure silicone. Third, the connecting ribbon may be laser tack welded to the battery.

Also not shown in FIG. 11 is the manner of connecting the proximal end of feed-through pin 702 to PC board 1002, and connecting a PC board ground pad to bottom case 710. An exemplary method of making these connections may be to use conductive epoxy and conductive ribbons, although other connection methods known in the art may also be used.

The layer of silicone molding 1104 may be used to cover all the surfaces of EA device 100 except for annular electrode 108 and central electrode 110. In certain examples, an over-molding process may be used to apply the layer of silicone molding 1104. For example, over-molding processes may be used such as: (a) molding a silicone jacket and gluing the jacket onto bottom case 710 using room temperature cure silicone (RTV) inside of a mold, and curing at room temperature; (b) injecting room temperature cure silicone in a mold formed from a material with excellent mechanical and/or chemical properties that are retained at high temperatures such that the silicone will not stick to the material (e.g., a PEEK or Teflon® mold); or (c) dip coating EA device 100 in room temperature cure silicone while masking the electrode surfaces that are not to be coated.

When assembled, insulating layer 1102 may be positioned underneath annular electrode 108 so that anode electrode 108 does not short to bottom case 710. As such, the only electrical connection made to the annular electrode 108 may be through the distal tip of feed-through pin 702. Similarly, the electrical contact with central electrode 110 may be made through bottom case 710. However, because EA device 100 may be coated with the layer of silicone molding 1104 everywhere besides annular electrode 108 and central electrode 110, all stimulation current generated by EA device 100 may be forced to flow between the exposed surfaces of the anode and cathode (i.e., between annular electrode 108 and central electrode 110).

As mentioned above, it will be understood that, while the configuration described herein uses annular electrode 108 as an anode electrode and central electrode 110 as a cathode electrode, this arrangement may be reversed in certain examples. For example, in certain implementations, the ring electrode (i.e., annular electrode 108) may serve as a cathode electrode while a circular, central electrode (i.e., central electrode 110) may serve as an anode electrode. Moreover, the location and shape of electrodes 108 and 110 may be configured differently than is shown in the implementations described above. For example, in certain implementations, annular electrode 108 may not be placed around the perimeter of the device, but rather may be a flat circumferential electrode that assumes different shapes (e.g., round or oval) and is placed on the front or back surface (i.e., bottom side 102 or top side 104) of EA device 100 so as to surround central electrode 110. Additionally, the same or other implementations, the surfaces of the anode and/or cathode electrodes (e.g., annular electrode 108 and/or central electrode 110) may have convex surfaces.

Moreover, while the implementation illustrated herein incorporates a round, short cylindrical-shaped housing (i.e., referred to as a "coin-shaped" housing), it will be understood that other implementations may employ different shapes for the container (e.g., bottom case 710), and/or the associated cover plate (e.g., cover plate 708). For example, bottom case 710 may be oval-shaped, rectangular-shaped (e.g., square with smooth corners), polygonal-shaped (e.g., hexagon-, octagon-, or pentagon-shaped), button-shaped (with convex top or bottom for a smoother profile), or shaped in any other way as may serve a particular implementation. Any of these alternate shapes, or others, would still permit EA device 100 to provide a robust, compact, thin, case to house the electronic circuitry and the power source used by EA device 100, would still help protect a feed-through assembly from being exposed to excessive heat during assembly, and would still allow the thin device to provide the benefits described herein related to its manufacture, implantation, and use. In particular, as long as EA device 100 remains relatively thin (e.g., less than approximately 2-3 mm) and does not have a maximum linear dimension greater than approximately 25 mm, EA device 100 may be readily implantable in a pocket over the tissue area where a selected acupoint (e.g., SP6, KI7, KI8, etc.) is located. Similarly, the principles described above in relation to recess cavity 802 may apply as long as there is a recess in the wall around the perimeter of bottom case 710 wherein the feed-through assembly may be mounted that effectively moves the wall or edge of bottom case 710 into the housing a safe thermal distance and a safe residual weld stress distance from the perimeter wall where a hermetically-sealed weld may occur.

Additionally, in some examples, central electrode 110 may be a shape other than round. For example, central electrode 110 may oval-shaped, polygonal-shaped, or shaped in another suitable way. While a round central electrode 110 may be approximately 4 mm across, a central electrode 110 taking another shape may have a size defined by a maximum width of the shape that may be any suitable size but may generally be less than approximately 7 mm.

In certain examples, the arrangement of the electrodes arrangement may be modified from the illustrations provided above. For example, as mentioned above, an electrode arrangement that utilizes a symmetrical electrode configuration (e.g., an annular electrode of a first polarity surrounding a central electrode of a second polarity) may make EA device 100 relatively immune to implantation in an improper orientation relative to the body tissue at the selected acupoint that is being stimulated. However, it will be understood that an electrode configuration that is not symmetrical may also be used in certain implementations. For example, two spaced-apart electrodes on a front surface of the housing, one of a first polarity, and a second of a second polarity, could still, when oriented properly with respect to a selected acupoint tissue location, provide desired therapeutic results.

To illustrate, FIG. 12 schematically illustrates exemplary alternative electrode configurations 1200 (e.g., electrode configurations 1200-1 through 1200-4) that may be used with EA device 100. As shown, each electrode configuration 1200 may include one or more central electrodes 1202 (e.g., central electrode 1202-1 in electrode configuration 1200-1, central electrode 1202-2 in electrode configuration 1200-2, central electrode array 1202-3 in electrode configuration 1200-3, and central electrode array 1202-4 in electrode configuration 1200-4). Additionally, each electrode configuration 1200 may include one or more annular electrodes 1204 (e.g., annular electrode 1204-1 in electrode configuration 1200-1, annular electrode array 1204-2 in electrode configuration 1200-2, annular electrode array 1204-3 in electrode configuration 1200-3, and annular electrode array 1204-4 in electrode configuration 1200-4).

As shown, electrode configurations 1200 may take various forms in different implementations. For example, electrode configuration 1200-1 schematically illustrates a single central electrode 1202-1 surrounded by a single annular electrode 1204-1. Electrode configuration 1200-1 is the same as the electrode configuration 1200-1 illustrated and described in relations to the figures above, and may be particularly advantageous due to its simplicity and symmetry.

Electrode configuration 1200-2 includes a single central electrode 1202-2 of one polarity surrounded by an oval-shaped electrode array 1204-2 including two electrodes having the opposite polarity. In certain examples, the oval-shape of electrode array 1204-2 could also be other shapes (e.g., circular, rectangular, square, etc.). Because the two electrodes of electrode array 1204-2 have the same polarity, when the two electrodes are properly aligned with body tissue being stimulated (e.g., aligned with a nerve underlying a desired acupoint), electrode configuration 1200-2 may stimulate the body tissue (e.g., the underlying nerve) at or near the desired acupoint with the same or similar efficacy achieved by electrode configuration 1200-1.

As used herein, the phrase "one or more electrodes" may be synonymous with the phrase "electrode or electrode array" and other similar phrases used herein. Moreover, it will be understood that, when a single electrode (e.g., one of electrodes 108 or 110) is described, the description may similarly apply to electrode arrays that include a plurality of electrodes. When an electrode array is referred to herein that comprises a plurality of individual electrodes of the same polarity, the individual electrodes of the same polarity within the electrode array may also be referred to as "individual electrodes," "segments" of the electrode array, or "electrode segments."

Electrode configuration 1200-3 includes a central electrode array 1202-3 that has three electrode segments of one polarity surrounded by an oval-shaped electrode array 1204-3 including three electrode segments having the opposite polarity. In certain examples, the oval-shape of electrode array 1204-3 could also be other shapes (e.g., circular, rectangular, square, etc.). In electrode configuration 1200-3, the three electrodes of electrode array 1204-3 may be positioned to be approximately equidistant from one another, although it may be difficult or impossible to position the electrodes perfectly equidistant from one another when electrode array 1204-3 is oval shaped as illustrated in FIG. 12. Fortunately, electrode array 1204-3 may stimulate the body tissue (e.g., the underlying nerve) at or near the desired acupoint with the same or similar efficacy achieved by electrode configuration 1200-1 even without perfectly symmetrical positioning of the electrode segments of electrode array 1204-3.

Similarly, electrode configuration 1200-4 includes a central electrode array 1202-4 that has four electrode segments of one polarity surrounded by an oval-shaped electrode array 1204-4 including four electrode segments having the opposite polarity. In certain examples, the oval-shape of electrode array 1204-4 could also be other shapes (e.g., circular, rectangular, square, etc.). In electrode configuration 1200-4, the four electrodes of electrode array 1204-4 may be positioned symmetrically, as shown, in a round or oval-shaped way. Electrode array 1204-4 may stimulate the body tissue (e.g., the underlying nerve) at or near the desired acupoint with the same or similar efficacy achieved by the other electrode configurations 1200 described above.

The electrode configurations 1200 shown schematically in FIG. 12 are only representative of a few electrode configurations that may be used with the present invention. In other examples, central electrodes and electrode arrays 1202 may not have the same number of electrode segments as the respective annular electrodes, and/or electrode arrays 1204 surrounding the central electrodes or electrode arrays 1202. For example, the respective central electrode or electrode array 1202 of a first polarity may include a single electrode, whereas the surrounding annular electrode or electrode array 1204 of a second polarity may have n individual electrode segments, where n is an integer that can vary from 1, 2, 3, . . . , n. Thus, for a circumferential electrode array where n=4, there may be four electrode segments of the same polarity arranged in circumferential pattern around a central electrode/array. If the circumferential electrode array with n=4 is a symmetrical electrode array, then the four electrode segments will be spaced apart equally in a circumferential pattern around a central electrode or electrode array. When n=1, the circumferential electrode array reduces to a single circumferential segment or a single annular electrode that surrounds a central electrode or electrode array.

Additionally, the polarities of the electrodes and electrode arrays may be selected as may serve a particular implementation. For example, while a central electrode or electrode array 1202 may typically be a cathode (i.e., representing a negative (−) polarity), and the surrounding electrode or electrode array 1204 may typically be an anode (i.e., representing a positive (+) polarity), these polarities may be reversed.

Moreover, it will also be understood that the shape of the circumferential electrode or electrode array (e.g., whether circular, oval, or any other shape) may not be the same shape as the housing of EA device 100 (e.g., bottom case 710. In particular, if the circumferential electrode or electrode array is not attached to a perimeter edge of the housing of EA device 100, the shape of the circumferential electrode or electrode array may be selected independently from the shape of the housing of EA device 100. As such, the housing of EA device 100 may be round (e.g., circular), oval-shaped, polygon-shaped, or shaped in any other way as may serve a particular implementation (e.g., based on the need and/or preferences of a particular manufacturer, physician, patient, etc.).

Next, the electrical design and operation of the circuits employed within EA device 100 will be described.

Figure 13A:
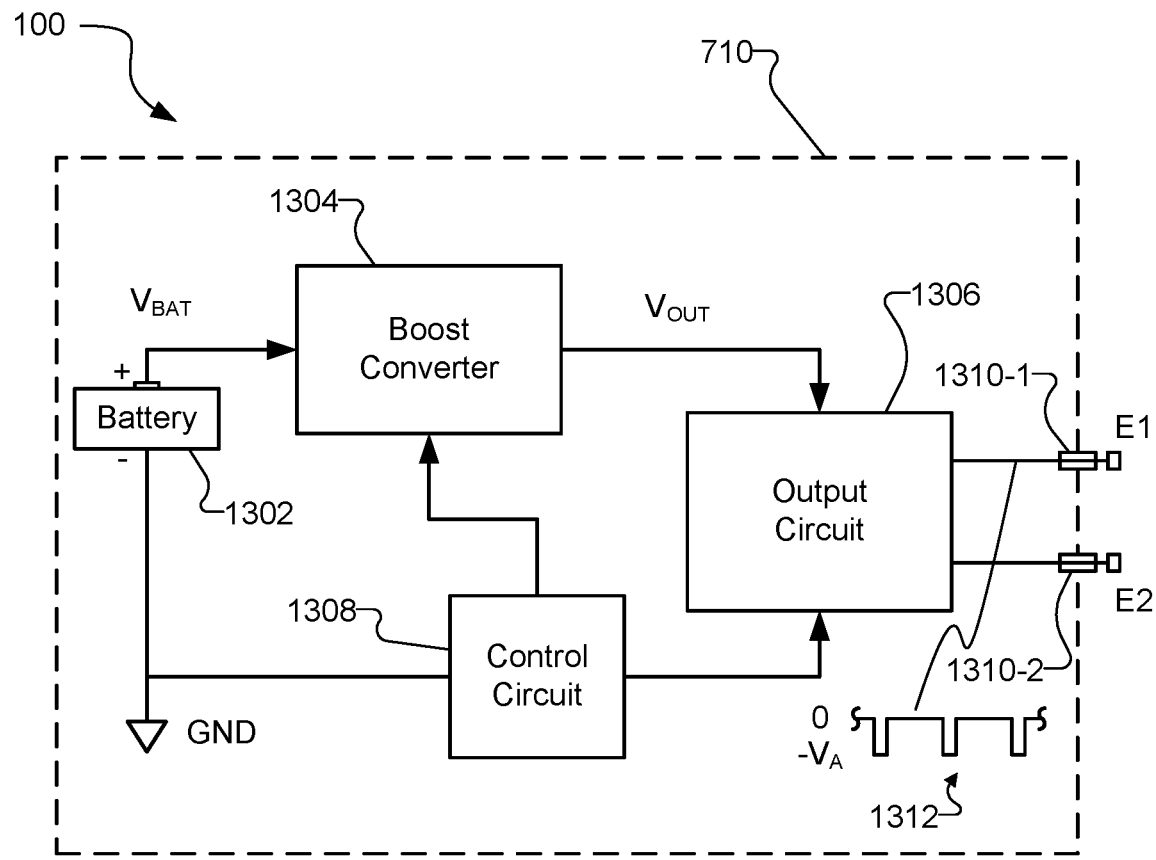
FIG. 13A illustrates an exemplary functional block diagram of the electronic circuits used within the EA device illustrated in FIG. 1 according to principles described herein.

FIG. 13A shows a functional block diagram of EA device 100. As seen in FIG. 13A, EA device 100 may use an implantable battery 1302 having a battery voltage $V_{BAT}$. For example, battery 1302 may be similar or identical to battery 706, described above. EA device 100 may also include a boost converter circuit 1304, an output circuit 1306 and a control circuit 1308. As described above, battery 1302, boost converter circuit 1304, output circuit 1306 and control circuit 1308 may all be housed within a hermetically sealed housing (e.g., including bottom case 710, described above).

As controlled by control circuit 1308, output circuit 1306 of EA device 100 may generate a sequence of stimulation pulses that are delivered to electrodes E1 and E2, through feed-through terminals 1310 (e.g., terminals 1310-1 and 1310-2), respectively, in accordance with a prescribed stimulation regimen. In some examples, a coupling capacitor $C_C$ (not explicitly shown in FIG. 13A) may also be employed in series with at least one of feed-through terminals 1310 to prevent direct current ("DC current") from flowing into the patient's body tissue.

As will be explained in more detail below in relation to FIGS. 15A and 15B, the prescribed stimulation regimen may include a continuous stream of stimulation pulses having a fixed amplitude, e.g., $V_A$ volts (also referred to as an amplitude A1), a fixed pulse width (e.g., 0.5 milliseconds), and a fixed frequency (e.g., 2 Hz) during each stimulation session. This is illustrated by waveform 1312 in FIG. 13A. In certain examples, the stimulation session, which may also be part of the stimulation regimen, may be generated at a very low duty cycle (e.g., for 30 minutes once each week). Additionally, other stimulation regimens may also be used such as a variable frequency stimulation regimen where the stimulus pulse during a stimulation session is a variable frequency rather than a fixed frequency. The rate of occurrence of the stimulation session may be varied as may serve a particular implementation. For example, stimulation session may occur as frequently as one or more times per day or may be as infrequent as once every 14 days or longer.

Electrodes E1 and E2 may form an integral part of the housing of EA device 100 (e.g., part of bottom case 710). For example, as described and illustrated above, electrode E2 may comprise a circumferential anode electrode (e.g., such as annular electrode 108, described and illustrated above) that surrounds a cathode electrode E1 (e.g., such as central electrode 110, also described and illustrated above). In certain examples, cathode electrode E1 may be electrically connected to bottom case 710 (thereby making feed-through terminal 1310-1 unnecessary). In the same or other implementations, anode electrode E2 may be electrically connected to bottom case 710 (thereby making feed-through terminal 1310-2 unnecessary).

In some examples, cathode electrode E1 may be electrically connected to the circumferential electrode that surrounds the anode electrode E2. That is, the stimulation pulses delivered to the target tissue location (i.e., to the selected acupoint) through electrodes E1 and E2 may be, relative to a zero volt ground (GND) reference, negative stimulation pulses, as shown in waveform 1312. Accordingly, as shown in FIG. 13A, electrode E2 may function as an anode, or positive (+), electrode, while electrode E1 may function as a cathode, or negative (−), electrode during a stimulation pulse.

Battery 1302 may provide all of the operating power needed by EA device 100. In certain examples, the battery voltage $V_{BAT}$ of battery 1302 may not be the optimum voltage needed by the circuits of EA device 100, including the output circuitry, in order to efficiently generate stimulation pulses of amplitude (e.g., $-V_A$ volts). Rather, the amplitude $V_A$ of the stimulation pulses may be many times greater than the battery voltage $V_{BAT}$. Accordingly, the battery voltage may need to be "boosted", or increased, in order for stimulation pulses of amplitude $V_A$ to be generated. Such "boosting" may be performed using boost converter circuit 1304. Thus, boost converter circuit 1304 may function to convert the input voltage (i.e., $V_{BAT}$) to an output voltage (i.e., $V_{OUT}$) used by output circuit 1306 in order for EA device 100 to properly function.

EA device 100 may advantageously provide a small, self-contained, coin-sized, coin-shaped stimulator that may be implanted in a patient at or near a specified acupoint in order to favorably treat a condition or disease of a patient. The coin-sized stimulator may apply electrical stimulation pulses at very low levels and low duty cycles in accordance with specified stimulation regimens through electrodes that form an integral part of the housing of the stimulator. Because of this, EA device 100 may include and be powered by a relatively small battery. An exemplary battery that may be included in EA device 100 is a coin-cell battery having a thickness that is less than or equal to 3 mm (e.g., 2.2 mm thick). This relatively small battery may fit within the coin-sized stimulator and provide enough energy for EA device 100 to perform a specified stimulation regimen over a period of several years. Thus, the coin-sized stimulator, once implanted, may provide an unobtrusive, needleless, long-lasting, safe, elegant, and effective mechanism for treating certain conditions and diseases that have long been treated by acupuncture or electroacupuncture.

Figure 13B:
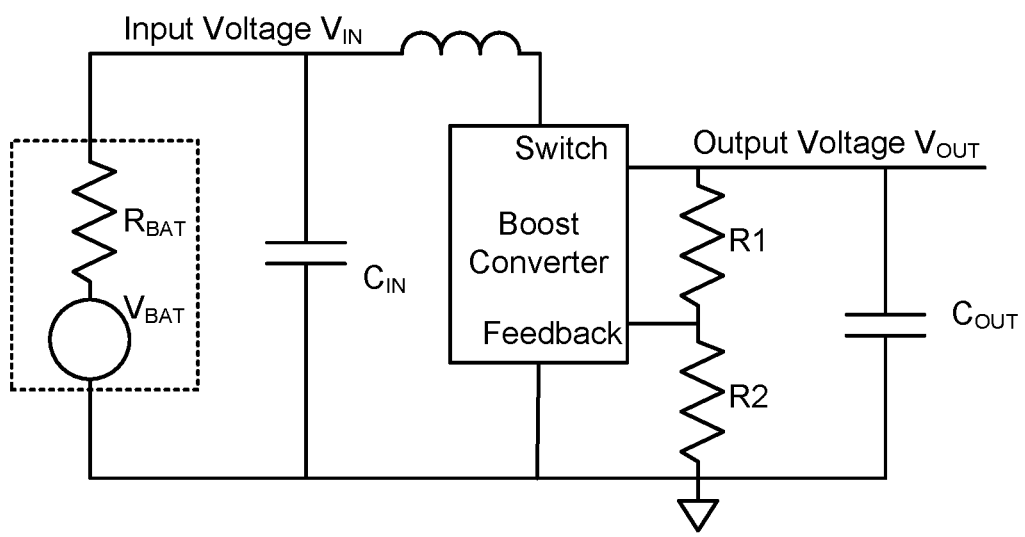
FIG. 13B illustrates an exemplary basic boost converter circuit configuration according to principles described herein.

A boost converter integrated circuit (IC) such as boost converter 1304 typically draws current from its power source in a manner that is proportional to the difference between the actual output voltage $V_{OUT}$ and a set point output voltage, or feedback signal. An exemplary boost converter circuit that operates in this manner is shown in FIG. 13B. At boost converter start up, when the actual output voltage is low compared to the set point output voltage, the current drawn from the power source can be quite large. Unfortunately, when batteries are used as power sources, the batteries may have internal voltage losses (caused by internal impedance of the batteries) that are proportional to the current drawn from the batteries. This can result in under voltage conditions when there is a large current demand from the boost converter at start up or at high instantaneous output current. Current surges and the associated under voltage conditions can lead to undesired behavior and reduced operating life of an implanted electro-acupuncture device such as EA device 100.

Figure 14:
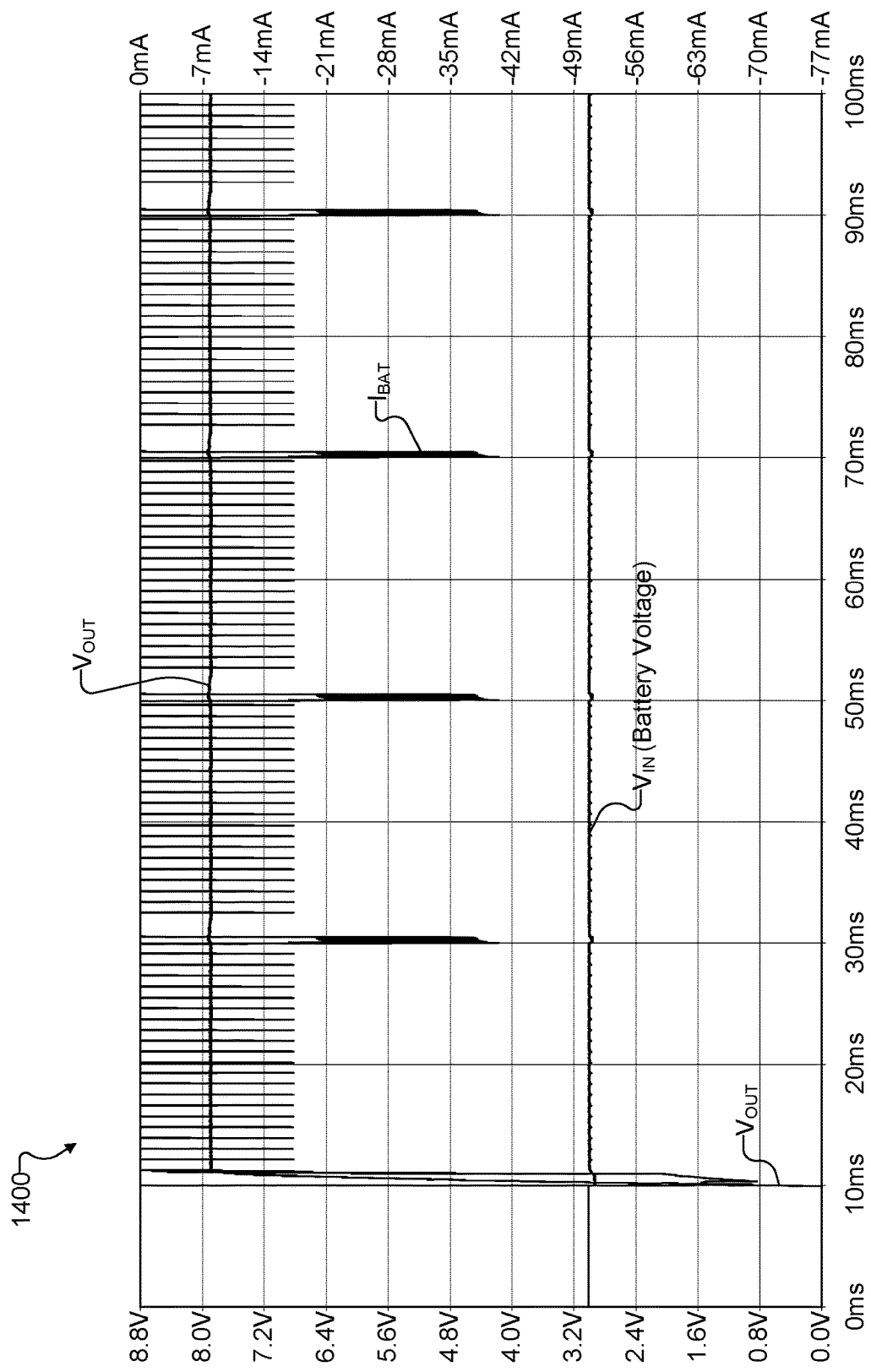
FIG. 14 illustrates an exemplary voltage and current waveform for the circuits of FIGS. 13A and 13B when the battery impedance is small according to principles described herein.

To illustrate, FIG. 14 illustrates an exemplary waveform 1400 illustrating an exemplary boost converter input voltage $V_{IN}$, an exemplary output voltage $V_{OUT}$, and an exemplary current drawn from the battery $I_{BAT}$. For example, in the boost converter circuit example shown in FIG. 13B, the battery is modeled as a voltage source with a simple series resistance. Exemplary waveform 1400 illustrates $V_{IN}$, $V_{OUT}$, and $I_{BAT}$ when series resistance $R_{BAT}$ (i.e., illustrated in FIG. 13A) is relatively small (e.g., approximately 5 ohms or less). In waveform 1400, the horizontal axis represents time, the vertical axis on the left represents voltage, and the vertical axis on the right represents current.

As illustrated by waveform 1400, at boost converter startup (10 ms), there may be 70 mA of current drawn from the battery with only approximately 70 mV of drop in input voltage $V_{IN}$. Similarly, the instantaneous output current demand for electro-acupuncture pulses may draw up to 40 mA from the battery with an input voltage drop of approximately 40 mV.

Figure 15:
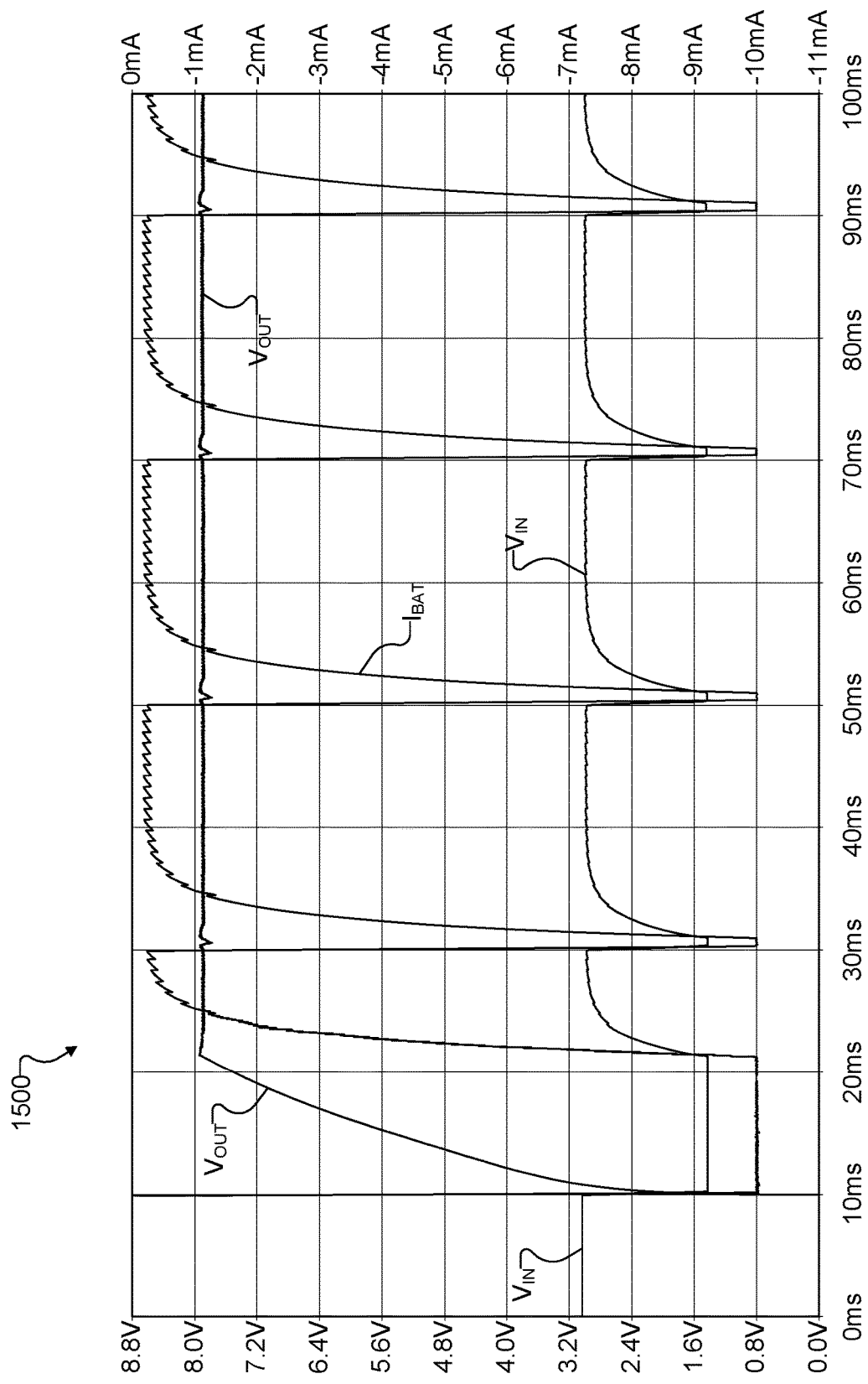
FIG. 15 illustrates an exemplary voltage and current waveform for the circuits of FIGS. 13A and 13B when the battery impedance is large according to principles described herein.

Disadvantageously, however, a battery with higher internal impedance (e.g., greater than 5 ohms and less than 250 ohms) may not be able to source more than about a milliampere of current without undergoing a significant drop in output voltage. To illustrate, FIG. 15 shows an exemplary waveform 1500 illustrating another exemplary boost converter input voltage $V_{IN}$, another exemplary output voltage $V_{OUT}$, and another exemplary current drawn from the battery $I_{BAT}$. As with FIG. 14, in FIG. 15 the horizontal axis represents time, the left vertical axis represents voltage, and the right vertical axis represents current.

As illustrated by waveform 1500, as a result of the higher internal battery impedance, the voltage at the battery terminal ($V_{IN}$) may be pulled down from 2.9 V to the minimum input voltage of the boost converter (approximately 1.5 V) during startup and during the instantaneous output current load associated with electro-acupuncture stimulus pulses. The resulting drops in output voltage $V_{OUT}$ may not be ideal or acceptable in certain types of circuit (e.g., circuits other than uncontrolled oscillator circuits).

Also, it will be understood that, although the battery used in the boost converter circuit is modeled in FIG. 13B as a simple series resistor, battery impedance can arise from the internal design, battery electrode surface area, and/or different types of electrochemical reactions. One or more of these contributors to battery impedance may cause the voltage of the battery at the battery terminals to decrease as the current drawn from the battery increases.

In a suitably small and thin implantable electroacupuncture device (e.g., EA device 100) of the type disclosed herein, it may be desirable to use a battery having a relatively high impedance in order to assure a small and thin device, keep costs low, and/or to have low self-discharge rates. In some examples, the battery internal impedance may increase as the battery discharges. This increase may limit the service life of the electroacupuncture device even if a new battery has acceptably low internal impedance. Thus, for EA device 100 to perform its intended function reliably over a long period of time, it may be desirable to incorporate a circuit design for the boost converter circuit that is capable of managing the instantaneous current drawn from $V_{IN}$ of the battery. Such current management may help prevent the internal impedance of the battery from causing $V_{IN}$ to drop to unacceptably low levels as the boost converter circuit pumps up the output voltage $V_{OUT}$, and/or when there is high instantaneous output current demand, as occurs when EA stimulation pulses are generated.

Figure 16:
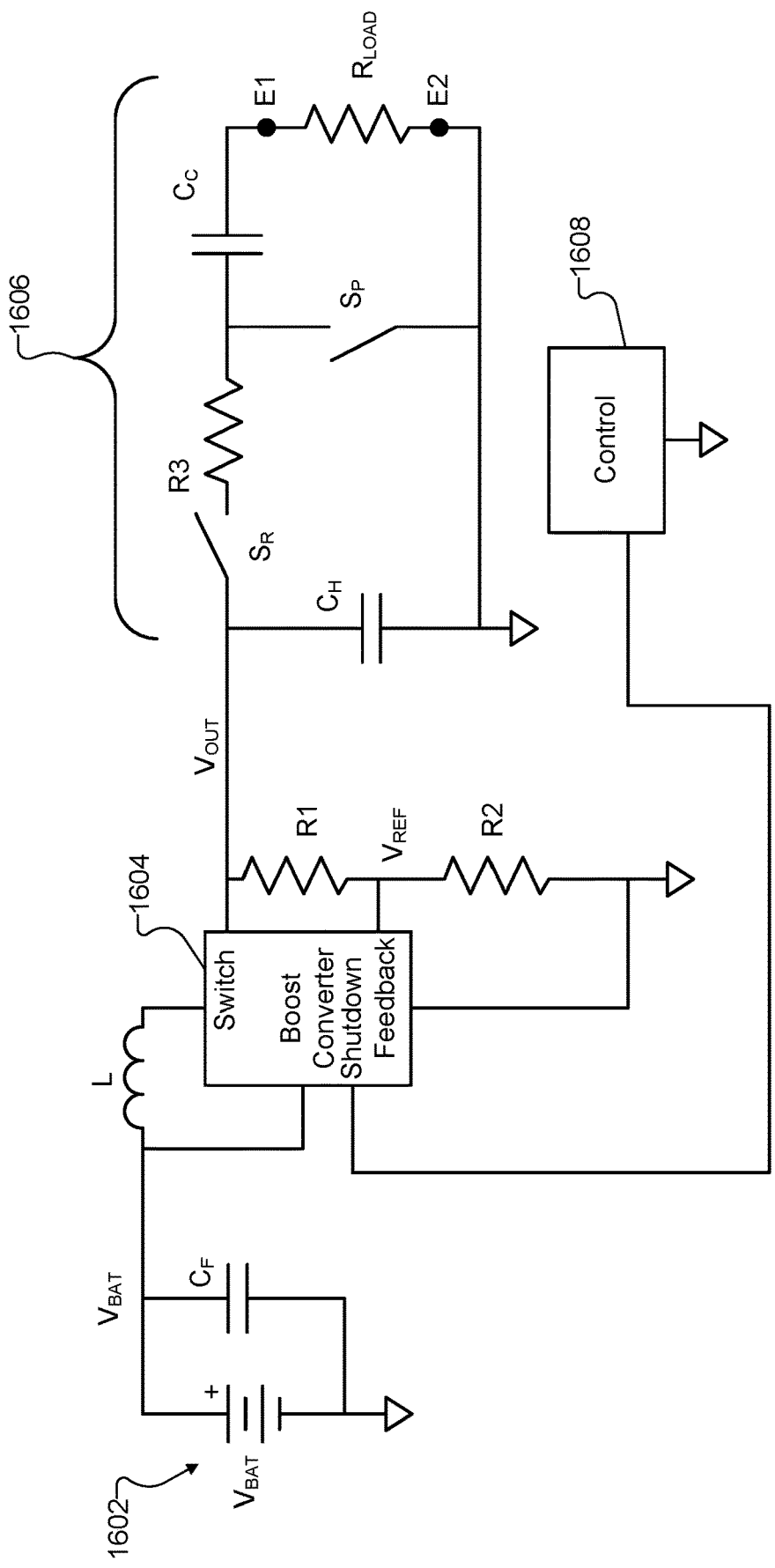
FIG. 16 illustrates an exemplary boost converter circuit and a functional pulse generation circuit configuration for use within the EA device illustrated in FIG. 1 according to principles described herein.

To provide this type of current management, EA device 100 may employ electronic circuitry as shown in FIG. 16, or an equivalent thereof. Similar to the circuitry shown in FIG. 13A, the circuitry of FIG. 16 includes a battery 1602, a boost converter circuit 1604, an output circuit 1606, and a control circuit 1608. In certain examples, control circuit 1608 may generate a digital control signal used to control a duty cycle of boost converter circuit 1604 between ON and OFF. By controlling the duty cycle in this way, control circuit 1608 may help limit the instantaneous current drawn from battery 1602. That is, the digital control signal may pulse the boost converter ON for a short time, but then may shut the boost converter down before a significant current can be drawn from battery 1602. In conjunction with such pulsing, an input capacitance $C_F$ is used to reduce the ripple in input voltage $V_{IN}$. For example, capacitor $C_F$ may supply the high instantaneous current for the short time that the boost converter is ON and then recharges more slowly from the battery during the interval that the boost converter is OFF.

In the circuitry shown in FIG. 16, it will be understood that the output voltage $V_{OUT}$ generated by the boost converter circuit 1604 may be set by the reference voltage $V_{REF}$ applied to the set point or feedback terminal of the boost converter circuit 1604. For the configuration shown in FIG. 16, $V_{REF}$ may be proportional to the output voltage $V_{OUT}$, as determined by the resistor dividing network of R1 and R2.

Additionally, switches $S_P$ and $S_R$, shown in FIG. 16 as part of the output circuit 1606, may also be controlled by control circuit 1608. Switches $S_P$ and $S_R$ may be selectively closed and opened to form the EA stimulation pulses applied to the load, represented by $R_{LOAD}$. For example, prior to a stimulus pulse, switch $S_R$ may be closed sufficiently long for the circuit side of coupling capacitor $C_C$ to be charged to output voltage $V_{OUT}$. The tissue side of $C_C$ may be maintained at 0 volts by cathode electrode E2, which may be maintained at ground reference. Then, for most of the time between stimulation pulses, both switches $S_R$ and $S_P$ may be kept open, with a voltage approximately equal to output voltage $V_{OUT}$ appearing across the coupling capacitor $C_C$.

At the leading edge of a stimulus pulse, the switch $S_P$ may be closed, immediately causing a negative voltage $-V_{OUT}$ to appear across $R_{LOAD}$ and causing the voltage at anode E1 to also drop to approximately $-V_{OUT}$, thereby creating the leading edge of the stimulus pulse. This voltage may start to decay back to 0 volts as controlled by an RC (resistor-capacitance) time constant that is long compared with the desired pulse width.

At the trailing edge of the pulse, before the voltage at anode E1 has decayed very much, the switch $S_P$ may be open and the switch $S_R$ may be closed. This action may cause the voltage at anode E1 to immediately (or quickly) return to 0 volts, thereby defining the trailing edge of the pulse. With the switch $S_R$ closed, the charge on the circuit side of the coupling capacitor $C_C$ may be allowed to charge back to $V_{OUT}$ within a time period controlled by a time constant set by the values of capacitor $C_C$ and resistor R3. When the circuit side of the coupling capacitor $C_C$ has been charged back to $V_{OUT}$, then switch $S_R$ may be opened, and both switches $S_R$ and $S_P$ may remain open until the next stimulus pulse is to be generated. The process described above may repeat each time a stimulus pulse is to be applied across the load.

Accordingly, FIG. 16 illustrates that, for a particular implementation of the electronic circuitry of EA device 100, a boost converter circuit 1604 may be employed which can be shut down with a control signal. The control signal may be a digital control signal generated by a control circuit 1608, which may be realized using a microprocessor or equivalent circuit as may serve a particular implementation. The control signal may be applied to the low side (ground side) of the boost converter circuit 1604 (i.e., labeled as the "shutdown" terminal in FIG. 16). Capacitor $C_F$ may supply instantaneous current for the short ON time that the control signal enables the boost converter circuit to operate, and may be recharged from battery 1602 during the relatively long OFF time when the control signal disables the boost converter circuit.

Figure 17:
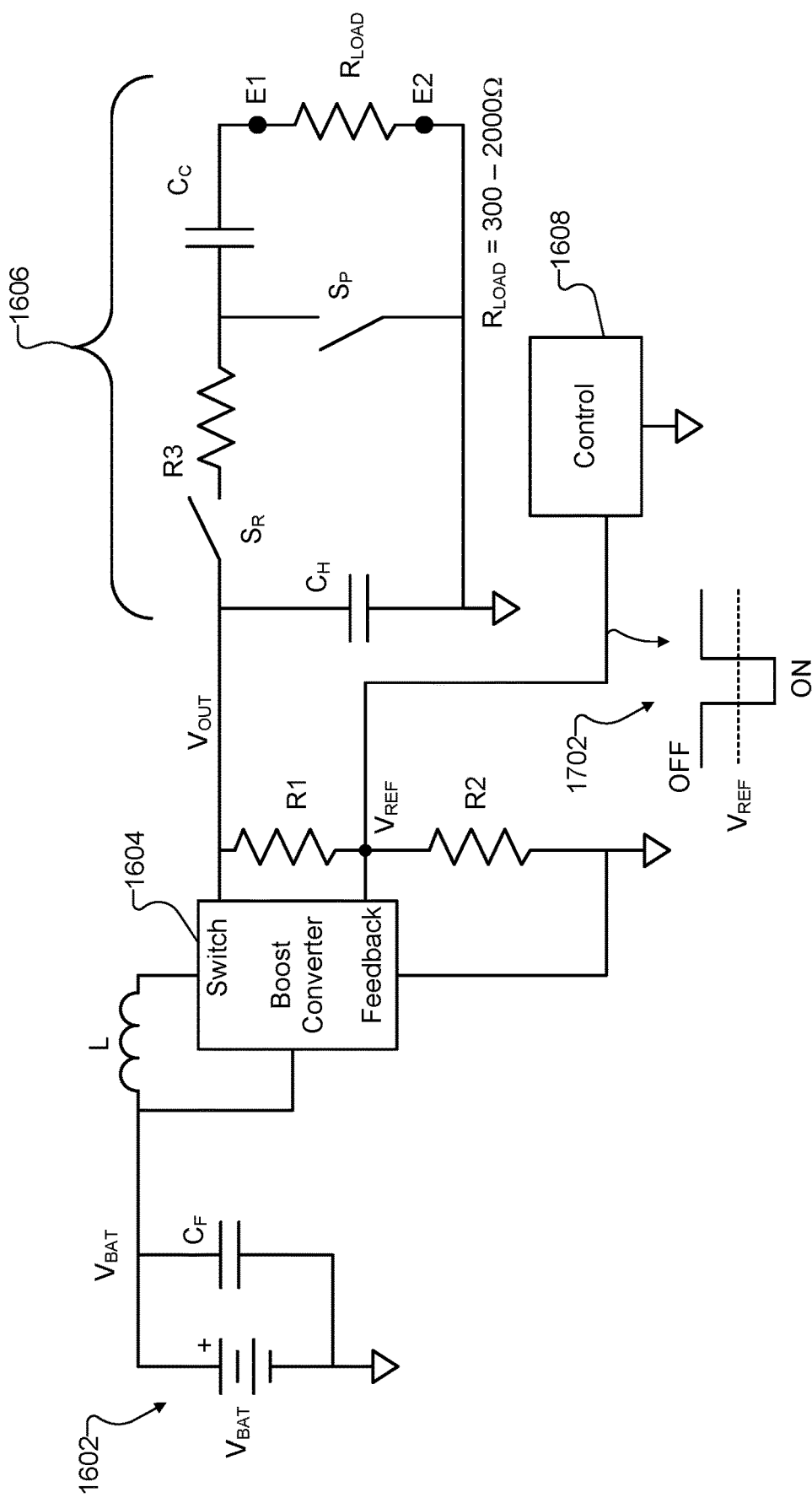
FIG. 17 illustrates an exemplary alternate boost converter circuit and an exemplary alternate functional pulse generation circuit for use within the EA device illustrated in FIG. 1 according to principles described herein.

FIG. 17 illustrates an alternate implementation of the electronic circuitry that may be used within EA device 100. As shown, the circuitry illustrated in FIG. 17 may be the same in many respects as the circuitry illustrated in FIG. 16. However, in FIG. 17, boost converter circuit 1604 does not have a specific shut down input control. Rather, as shown, boost converter circuit may be shut down by applying a control voltage to the feedback input of the boost converter circuit 1604 that is higher than $V_{REF}$. When the control voltage applied to the feedback input of boost converter 1604 is greater than $V_{REF}$, boost converter 1604 may stop switching and draw little or no current from battery 1602. In some examples, the value of $V_{REF}$ may be a low enough voltage (e.g., a 1.2 V band-gap voltage) that a low level digital control signal may be used to disable boost converter circuit 1604. To enable boost converter circuit 1604, the control signal may be set to go to a high impedance, which may effectively return the node at the $V_{REF}$ terminal to the voltage set by the resistor divider network formed from R1 and R2. Alternatively, the control signal may be set to go to a voltage less than $V_{REF}$.

At the output of control circuit 1608, an exemplary low level digital control signal 1702 is illustrated. Control signal 1702 may perform the function of enabling (turning ON) or disabling (turning OFF) boost converter circuit 1604 in accordance with the techniques described above. The signal line on which this control signal is present connects the output of control circuit 1608 with the $V_{REF}$ node connected to the feedback input of the boost converter circuit. As illustrated by the waveform of control signal 1702, control signal 1702 may vary from a voltage greater than $V_{REF}$ (thereby disabling or turning OFF the boost converter circuit) to a voltage less than $V_{REF}$ (thereby enabling or turning the boost converter circuit ON).

Figure 18:
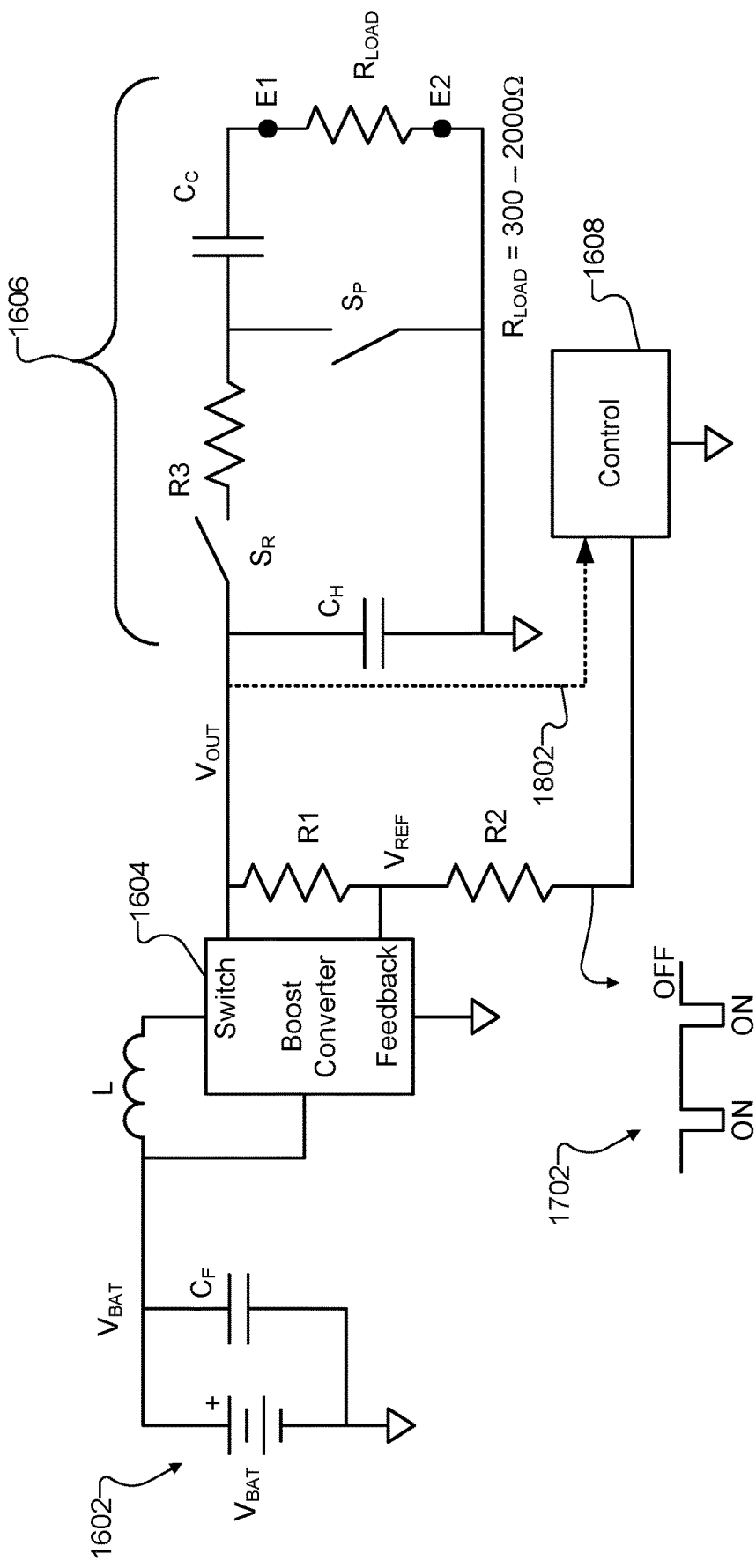
FIG. 18 illustrates an exemplary refinement of the circuit configuration of FIG. 17 according to principles described herein.

In certain examples, control signal 1702 may be used to drive the low side of R2. To illustrate, FIG. 18 shows control signal 1702 connected to the low side of R2, which is in turn connected to the $V_{REF}$ node. As such, in FIG. 18, boost converter circuit 1604 may be shut down when control signal 1702 is greater than $V_{REF}$ and may run when control signal 1702 is less than $V_{REF}$. A digital control signal can be used to perform this function by switching between ground and a voltage greater than $V_{REF}$. Additionally, the implementation of FIG. 18 presents the possibility of delta-sigma modulation control of $V_{OUT}$ if a measurement of the actual $V_{OUT}$ is available for feedback (e.g., using a signal line 1802) to the controller.

Figure 19:
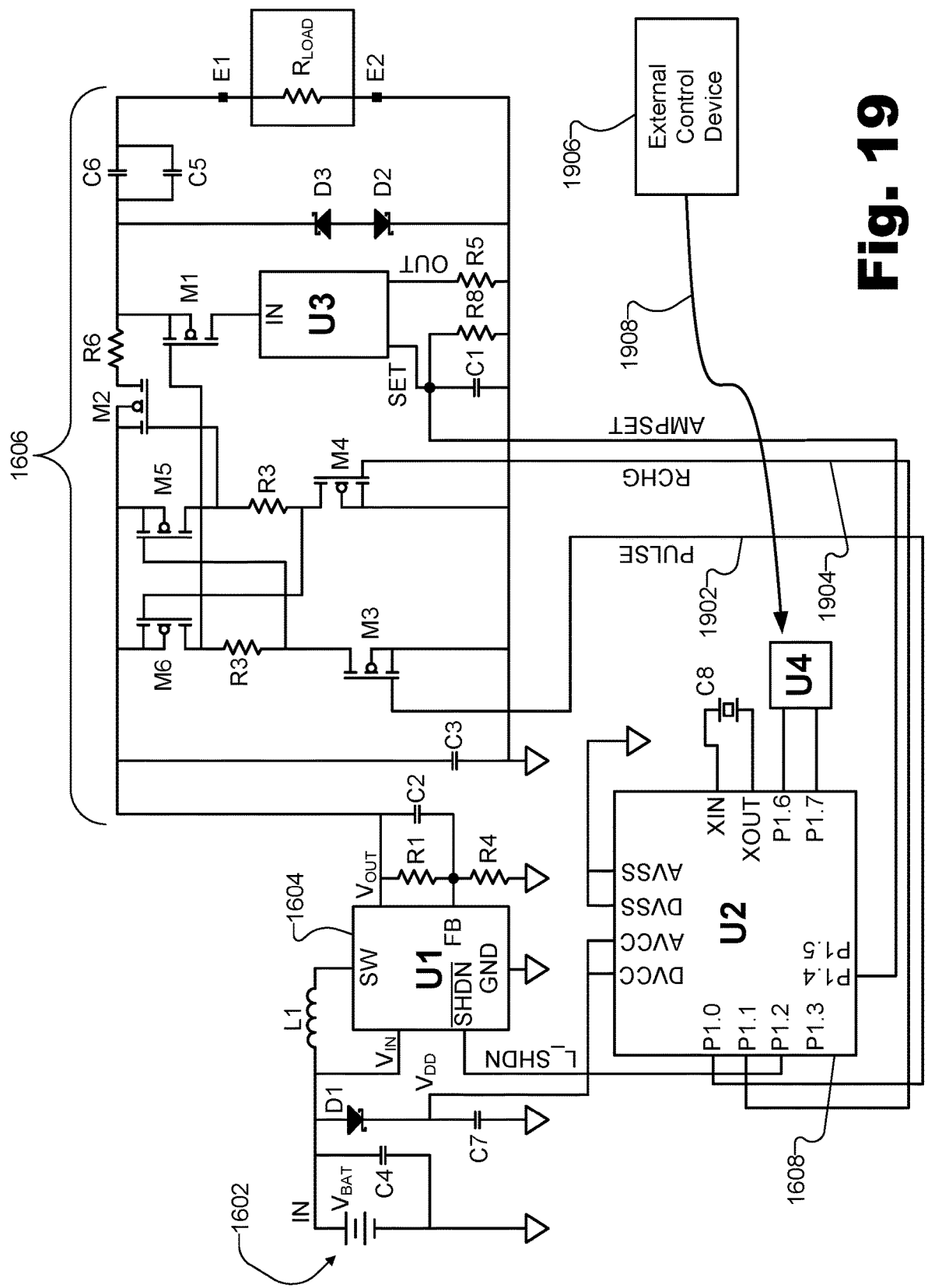
FIG. 19 illustrates an exemplary schematic configuration for the EA device illustrated in FIG. 1 that utilizes the boost converter configuration shown in FIG. 16 according to principles described herein.

FIG. 19 illustrates a schematic diagram of an exemplary embodiment of the circuitry described above used in an implantable electroacupuncture device such as EA device 100. In FIG. 19, the circuitry may employ a digital control signal as described above in relation to control signal 1702. As shown, FIG. 19 includes four integrated circuits ("ICs") used as the main components. The IC labeled "U1" ("IC U1") represents boost converter circuit 1604 and may perform the function described above in relation to boost converter circuit 1604. The IC labeled "U2" ("IC U2" or "microcontroller U2") represents control circuit 1608, which may be implemented by a microcontroller IC configured to perform the function of control circuit 1608 described above in relation to control circuit 1608.

In some examples, the microcontroller IC used to implement control circuit 1608 may include internal memory (e.g., 8 KB or any other amount of Flash memory). Having memory included with the microcontroller may be advantageous because the memory may allow the parameters associated with a selected stimulation regimen to be defined and stored. In some examples, EA device 100 may provide a stimulation regimen defined with a small number of parameters (e.g., five parameters). Accordingly, the programming features of the microcontroller may be carried out in a simple and straightforward manner.

As described above in relation to control circuit 1608, microcontroller U2 may primarily perform the function of generating the digital signal that shuts down boost converter circuit 1604 (i.e. IC U1) to prevent too much instantaneous current from being drawn from battery 1602. Microcontroller U2 may also control the generation of the stimulus pulses at the desired pulse width and frequency, and may further keep track of the time periods associated with a stimulation session (e.g., when a stimulation session begins and when the stimulation session ends).

Microcontroller U2 may also control the amplitude of the stimulus pulse. This may be performed by adjusting the value of a current generated by a programmable current source IC labeled "U3" ("IC U3" or "current source U3"). In one embodiment, IC U3 may be implemented using a voltage controlled current source IC. In such a voltage controlled current source, the programmed current may be set by a programmed voltage appearing across a fixed resistor R5 (i.e., the voltage appearing at the "OUT" terminal of IC U3). This programmed voltage, in turn, may be set by the voltage applied to the "SET" terminal of IC U3. That is, the programmed current source U3 may set the voltage at the "OUT" terminal to be equal to the voltage applied to the "SET" terminal. The programmed current that flows through resistor R5 may then be set by Ohm's Law to be the voltage at the "set" terminal divided by R5. As the voltage at the "set" terminal changes, the current flowing through resistor R5 at the "OUT" terminal changes, and this current may essentially be the same as the current pulled through the closed switch M1, which is essentially the same current flowing through the load $R_{LOAD}$. Hence, whatever current flows through resistor R5, as set by the voltage across resistor R5, may be essentially the same current that flows through the load $R_{LOAD}$. Thus, as control circuit 1608 (i.e., microcontroller U2) sets the voltage at the "set" terminal of current source U3 (i.e., the signal on the signal line labeled "AMPSET"), control circuit 1608 may control what current flows through the load $R_{LOAD}$. It will be understood that the amplitude of the voltage pulse developed across the load $R_{LOAD}$ may not exceed the voltage $V_{OUT}$ developed by boost converter circuit 1604 less the voltage drops across the switches and current source.

The switches $S_R$ and $S_P$ described previously in connection with FIGS. 16, 17, and 18 may be implemented in any suitable way as may serve a particular implementation. For example, as shown in FIG. 19, switches $S_R$ and $S_P$ may be implemented by transistor switches M1, M2, M3, M4, M5 and M6, each of which may be controlled directly or indirectly by control signals generated by control circuit 1608 (i.e., microcontroller U2). For the embodiment shown in FIG. 19, these switches are controlled by two signals, one appearing on a signal line 1902 (i.e., labeled "PULSE"), and the other appearing on a signal line 1904 (i.e., labeled "RCHG," which is an abbreviation for "recharge"). For the circuit configuration shown in FIG. 19, the RCHG signal on signal line 1904 may always be the inverse of the PULSE signal appearing on signal line 1902. This type of control does not allow both switch M1 and switch M2 to be open or closed at the same time. Rather, switch M1 may always be closed when switch M2 is open, and switch M2 may always be closed when switch M1 is open. Accordingly, when switch M1 is closed, and switch M2 is open, the stimulus pulse appears across the load, $R_{LOAD}$, with the current flowing through the load, $R_{LOAD}$, being essentially equal to the current flowing through resistor R5. In contrast, when the switch M1 is open, and switch M2 is closed, no stimulus pulse appears across the load, and the coupling capacitors C5 and C6 are recharged through the closed switch M2 and resistor R6 to the voltage $V_{OUT}$ in anticipation of the next stimulus pulse.

The circuitry shown in FIG. 19 may be exemplary of one type of circuit that may be used to control the pulse width, amplitude, frequency, and duty cycle of stimulation pulses applied to the load, $R_{LOAD}$. However, it will be understood that any type of circuit, or control, that allows stimulation pulses of a desired magnitude (measured in terms of pulse width, frequency and amplitude, where the amplitude may be measured in current or voltage) to be applied through the electrodes to the patient at the specified acupoint at a desired duty cycle (i.e., stimulation session duration and frequency) may be used as may serve a particular implementation. Regardless, in order for the circuitry to properly function over a long period of time (e.g., several years) using only a small energy source such that provided by a coin-sized battery having a high battery impedance and a relatively low capacity, the circuitry must be properly managed and controlled to prevent excessive current draw from the battery.

Additionally, it may be important for the circuitry used in EA device 100 (e.g., the circuitry shown in FIGS. 16-19 or equivalents thereof) to include a means for controlling the stimulation current that flows through the load, $R_{LOAD}$, which may be characterized as the patient's tissue impedance at and around an acupoint being stimulated. As illustrated in FIGS. 17 and 18, the tissue impedance may vary from between about 300 ohms to 2000 ohms in certain examples. Moreover, the tissue impedance may not only vary from one patient to another, but may also vary within a given patient over time. Hence, EA device 100 may carefully control current that flows through $R_{LOAD}$ as the load varies. To this end, EA device 100 may control the stimulation current, as opposed to the stimulation voltage, so that the same current will flow through the tissue load regardless of changes that may occur in the tissue impedance over time. The use of a voltage controlled current source such as IC U3 shown in FIG. 19, is one way to perform this current control.

As further illustrated in FIG. 19, a fourth IC labeled "U4" ("IC U4" or "magnetic sensor U4") is connected to control circuit 1608 (i.e., microcontroller U2). In some examples, IC U4 may include an electromagnetic field sensor, and may allow the presence of an externally-generated (i.e., non-implanted) electromagnetic field to be sensed. An "electromagnetic" field, as used herein, may include any magnetic field, radio frequency (RF) field, light field, or the like. The electromagnetic sensor may take any form as may serve a particular implementation. For example, the electromagnetic sensor may include a wireless sensing element (e.g., a pickup coil or RF detector), a photon detector, a magnetic field detector, or another suitable electromagnetic sensor.

In certain implementations where a magnetic sensor is employed as the electromagnetic sensor of IC U4, the magnetic field may be generated using an external control device ("ECD") 1906 that may communicate wirelessly (e.g., through the presence or absence of a magnetic field), with the electromagnetic sensor of IC U4. For example, a wavy line 1908 in FIG. 19 may represent a magnetic field, or another type of field if a magnetic field is not used. In its simplest form, ECD 1906 may simply be a magnet, and modulation of the magnetic field may be achieved simply by placing or removing the magnet next to or away from EA device 100. When other types of sensors (e.g., non-magnetic sensors) are employed, ECD 1906 may generate an appropriate signal or field to be sensed by the sensor that is used.

Use of ECD 1906 may provide a way for the patient, or for medical personnel, to control EA device 100 before or after EA device 100 has been implanted with simple commands such as commands causing EA device 100 to be turned ON, to be turned OFF, to increase the amplitude of the stimulation pulses by one increment, to decrease the amplitude of the stimulation pulses by one increment, and so forth. In certain implementations, a simple coding scheme may be used to differentiate one command from another. For example, one coding scheme may be time-based. Specifically, a first command may be communicated by holding a magnet near EA device 100, and hence near magnetic sensor U4 contained within EA device 100, for differing lengths of time. If, for example, the magnet is held over EA device 100 for at least 2 seconds, but no more than 7 seconds, a first command may be communicated, while if the magnet is held over EA device 100 for at least 11 seconds, but no more than 18 seconds, a second command may be communicated, and so forth.

An alternative coding scheme that may be used is a sequence-based coding scheme. Specifically, an application of three magnetic pulses may be used to signal one external command if the sequence is repeated 3 times. A sequence of two magnetic pulses, repeated twice, may be used to signal another external command. A sequence of one magnetic pulse, followed by a sequence of two magnetic pulses, followed by a sequence of three magnetic pulses, may be used to signal yet another external command.

Other simple coding schemes may also be used, such as the letters AA, RR, HO, BT, KS using international Morse code. That is, the Morse code symbols for the letter "A" are dot dash, where a dot is a short magnetic pulse, and a dash is a long magnetic pulse. Thus, to send the letter A to EA device 100 using an external magnet, the user would hold the magnet over the area where EA device 100 is implanted for a short period of time (e.g., one second or less), followed by holding the magnet over EA device 100 for a long period of time (e.g., more than one second).

More sophisticated magnetic coding schemes may be used to communicate the operating parameters of EA device 100. For example, using an electromagnet controlled by a computer, the pulse width, frequency, and amplitude of the EA stimulation pulses used during each stimulation session may be pre-set. Also, the frequency of the stimulation sessions may be pre-set and/or a master reset signal may be sent to the device in order to re-set these parameters to default values. These same operating parameters and commands may be re-sent at any time to EA device 100 during the useful lifetime of EA device 100 should changes in the parameters be desired or needed.

Figure 20:
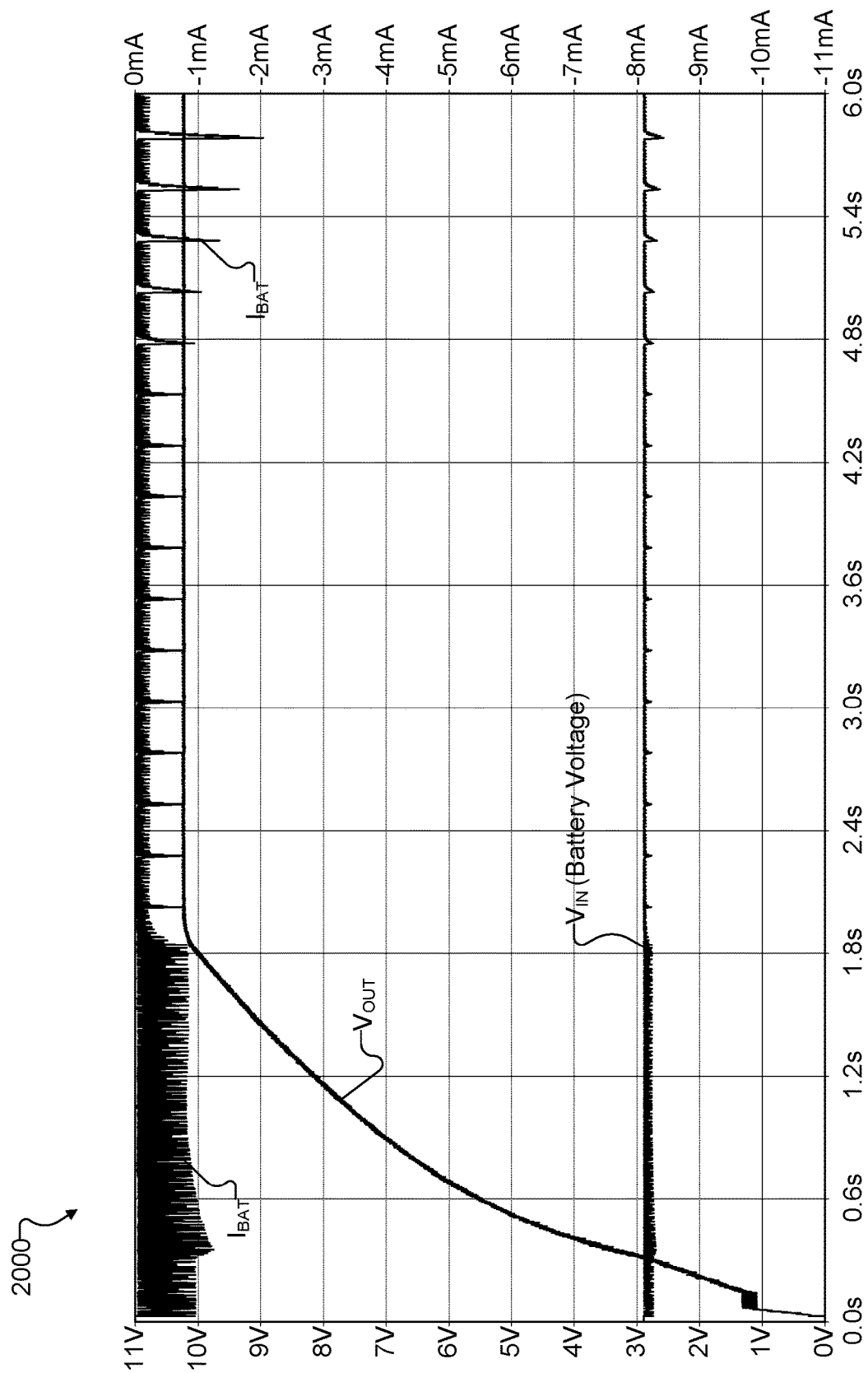
FIG. 20 illustrates exemplary current and voltage waveforms associated with the operation of the circuit shown in FIG. 19 according to principles described herein.

FIG. 20 illustrates current and voltage waveforms associated with the operation of the circuitry of EA device 100 shown in FIG. 19. In FIG. 20, the horizontal axis represents time, the left vertical axis represents voltage, and the right vertical axis represents current. The battery in the example of FIG. 20 may have approximately 160 ohms of internal impedance.

Referring to FIGS. 19 and 20, during startup, the ON time of boost converter circuit 1604 may be approximately 30 microseconds applied every 7.8 milliseconds. As shown, this ON time may be sufficient to ramp the output voltage $V_{OUT}$ up to over 10 V within 2 seconds while drawing no more than approximately 1 mA from battery 1602 and while inducing only approximately 150 mV of input voltage ripple.

The electroacupuncture simulation pulses generated by the circuitry shown in FIG. 19 may have a pulse width of approximately 0.5 milliseconds and may increase in amplitude from approximately 1 mA in the first pulse to approximately 15 mA in the last pulse. The instantaneous current drawn from battery 1602 may be less than approximately 2 mA for the electroacupuncture stimulation pulses and the drop in battery voltage may be less than approximately 300 mV. Boost converter circuit 1604 may be enabled (i.e., turned ON) only during the instantaneous output current surges associated with the 0.5 milliseconds wide EA pulses.

Figure 21:
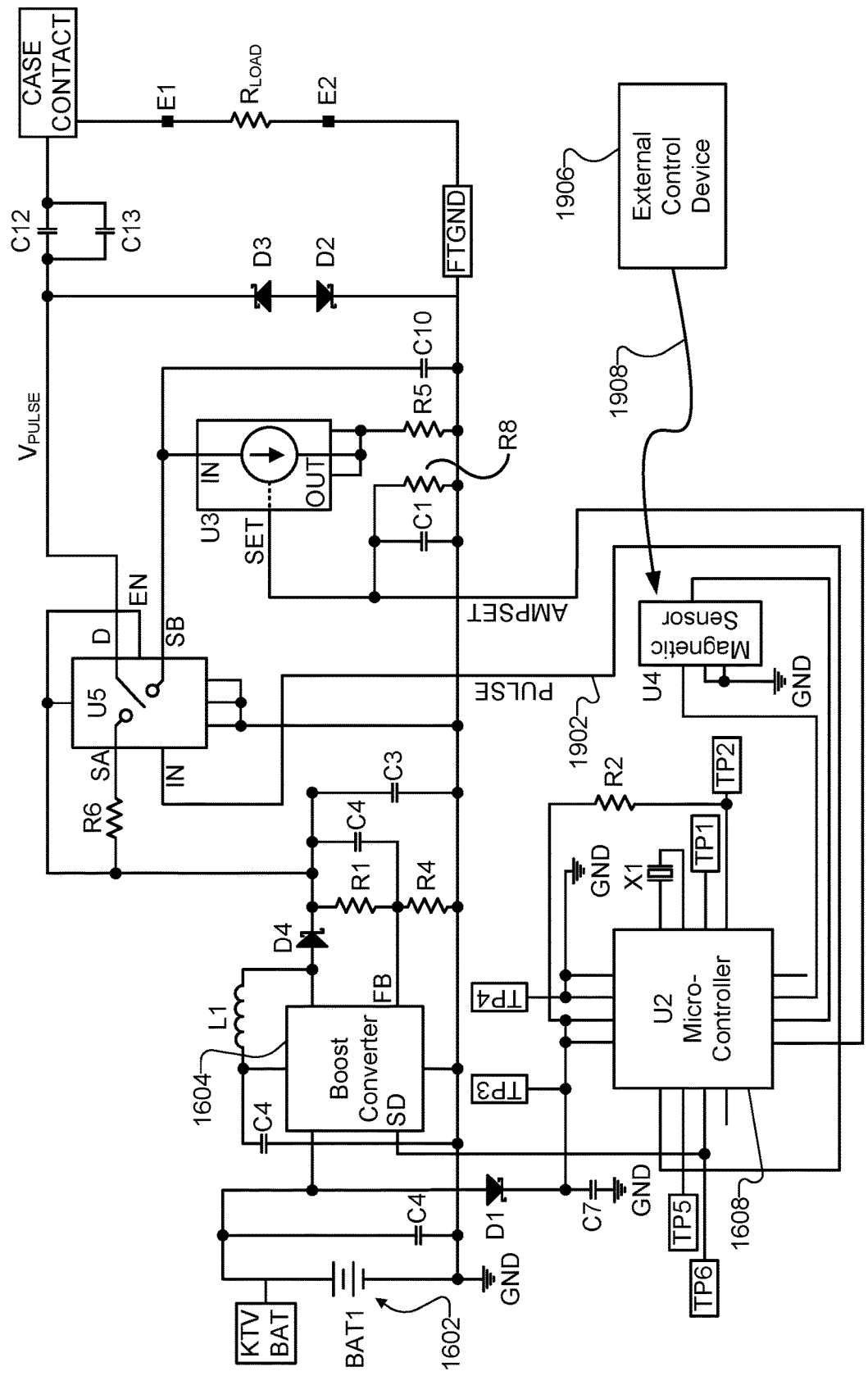
FIG. 21 illustrates another exemplary schematic configuration for the EA device illustrated in FIG. 1 similar to the configuration illustrated in FIG. 19, but which uses an alternate output circuitry configuration for generating the stimulus pulses according to principles described herein.

FIG. 21 illustrates another implementation of the circuitry that may be used in an implantable electroacupuncture device such as EA device 100. More specifically, FIG. 21 illustrates a schematic diagram of circuitry that employs a digital control signal as described above. The circuit shown in FIG. 21 is, in most respects, similar to the circuit described previously in connection with FIG. 19. However, FIG. 21 also includes a Schottky diode D4 at the output terminal of boost convertor circuit 1604 (i.e., IC U1), and includes a fifth IC labeled "U5" ("IC U5") that may perform the same or a similar function as described above in relation to switches M1-M6, shown in FIG. 19.

The Schottky diode D4 may help isolate output voltage $V_{OUT}$ generated by boost converter circuit 1604. In certain implementations, this isolation may facilitate boost converter circuit 1604 in providing an output voltage $V_{OUT}$ that is four or five times greater than the battery voltage $V_{BAT}$. For example, in the example of FIG. 21, output voltage $V_{OUT}$ may be designed to be approximately 15 volts where battery 1602 has a battery voltage of only approximately 3 volts. In contrast, the circuit in the example of FIG. 19 may be designed to provide an output voltage of approximately 10-12 volts where battery 1602 has a battery voltage of 3 volts.

IC U5 may be used to perform the function of a switch. The other ICs shown in FIG. 21 (i.e., boost converter circuit 1604 (IC U1), control circuit 1608 (microcontroller U2), current source U3, and electromagnetic sensor U4) may basically be the same described above in relation to FIG. 19.

More specifically, IC U5 may be configured to function as a single pole/double throw ("SPDT") switch. Numerous commercially available ICs may be used for this function. For example, an ADG1419 IC, available from Analog Devices Incorporated (ADI) may be used. In the ADG1419 IC, the terminal "D" may function as the common terminal of the switch, and the terminals "SA" and "SB" may function as the selected output terminal of the switch. The terminals "IN" and "EN" may be control terminals to control the position of the switch. Thus, when a signal present is on the PULSE line, which is connected to the "IN" terminal of the IC, the SPDT switch of the IC may connect the "D" terminal to the "SB" terminal, and may effectively connect cathode electrode E1 to the programmable current source IC (i.e., IC U3). This connection may cause the programmed current set by the control voltage AMPSET applied to the SET terminal of the programmable current source IC, to flow through resistor R5, which in turn may cause essentially the same current to flow through the load present between the electrodes E1 and E2 (i.e., $R_{LOAD}$). When a signal is not present on the PULSE line, the SPDT switch (i.e., IC U5) may effectively connect cathode electrode E1 to resistor R6, which may allow coupling capacitors C12 and C13 to recharge back to voltage $V_{OUT}$ provided by boost converter circuit 1604.

Figure 22:
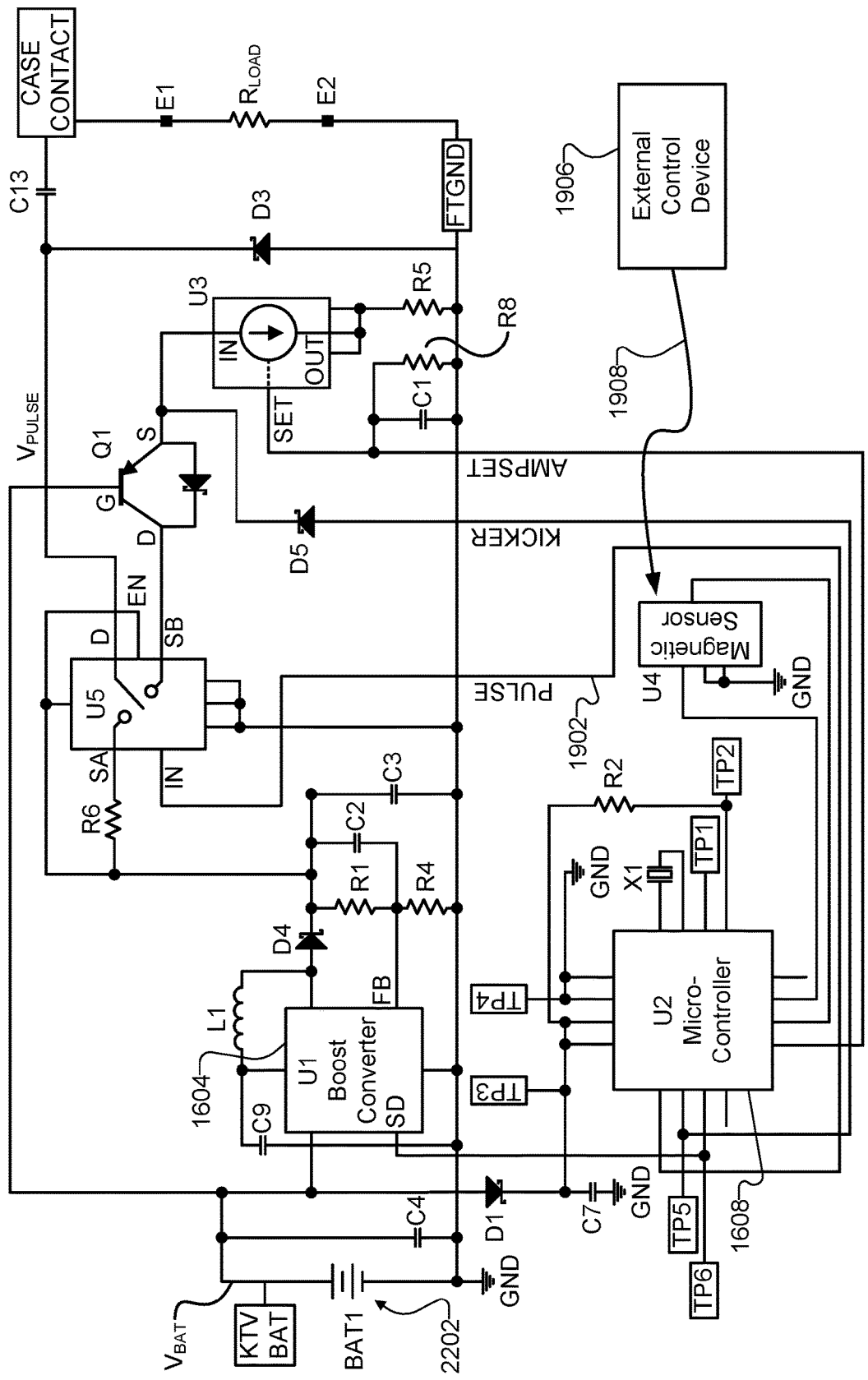
FIG. 22 illustrates yet a further exemplary schematic configuration for the EA device illustrated in FIG. 1 similar to configurations illustrated in FIGS. 19 and 21, but which includes additional enhancements and circuit features according to principles described herein.

FIG. 22 illustrates an exemplary schematic diagram of yet another implementation of circuitry that may be used in an implantable electroacupuncture device such as EA device 100. As shown, the circuitry in FIG. 22 may employ an ON-OFF approach to modulate a duty-cycle of boost converter circuit 1604 in order to limit the amount of instantaneous battery current drawn from a high impedance battery 2202. In most respects, the circuitry shown in FIG. 22 may be similar or the same as the circuitry described previously in relation FIG. 19. However, as will be described, the circuitry in FIG. 22 may also include additional elements and features that address additional issues associated with the operation of EA device 100.

For example, one feature included in the circuitry of FIG. 22 is that boost converter circuit 1604 (i.e., IC U1) may be modulated ON and OFF using digital control generated within boost converter circuit 1604 itself. Accordingly, boost converter circuit 1604 may shut itself down whenever the battery voltage falls below a predetermined level above that required by the remaining circuitry. For example, in the implementation shown in FIG. 22, boost converter circuit 1604 may be implemented by a MAX8570 boost converter IC, commercially available from Maxim, or equivalents thereof. The MAX8570 boost converter IC may shut down when the applied voltage $V_{BAT}$ falls below 2.5 V. However, a battery voltage of 2.5 volts is still high enough to ensure that control circuit 1608 (i.e., microcontroller U2), and other circuitry associated with the operation of the EA device 100, remain operational.

Thus, in operation, as soon as battery voltage $V_{BAT}$ drops below 2.5 volts, boost converter circuit 1604 may shut down, thereby limiting the instantaneous current drawn from the battery. When boost converter circuit 1604 shuts down, the instantaneous battery current drawn from the battery may be reduced (e.g., immediately reduced) by a significant amount, thereby causing battery voltage $V_{BAT}$ to increase.

As battery voltage $V_{BAT}$ increases, boost converter circuit 1604 may remain shut down until control circuit 1608 determines that it is time to turn boost converter circuit 1604 back ON. Control circuit 1608 may cause converter circuit 1604 to be turned back ON in any suitable way. For example, just prior to the delivery of the next stimulus pulse, a turn ON signal may be applied to the shutdown ("SD") terminal of boost converter circuit 1604. As another example, as soon as battery voltage $V_{BAT}$ has increased by a sufficient amount (e.g., as sensed at feedback terminal FB of boost converter circuit 1604), the circuits within boost converter circuit 1604 may automatically be turned back ON, allowing output voltage $V_{OUT}$ to build up to a voltage level needed by the switch circuit IC (i.e., IC U5) and the current source circuit IC (i.e., IC U3) to generate an output stimulus pulse of the desired amplitude when the next PULSE signal is applied to the IN terminal of the switch circuit IC by control circuit 1608 (i.e., microcontroller U2).

Once turned ON, boost converter circuit 1604 may remain ON until the input voltage again drops below 2.5 volts. This pattern may continue, with the boost converter being ON for a short time, and OFF for a much longer time (e.g., with a ON/OFF duty cycle no greater than approximately 0.01). In this way, the amount of current drawn from battery 2202 may be effectively controlled and limited even while ensuring that battery voltage $V_{BAT}$ always remains sufficiently high to permit operation of all circuitry of EA device 100 other than boost converter circuit 1604 (e.g., circuitry within microcontroller U2 of control circuit 1608).

The microcontroller of control circuit 1608 (i.e., IC U2), the current source circuit IC (i.e., IC U3), the sensor circuit IC (i.e., IC U4), and the switch circuit IC (i.e., IC U5) may each be implemented by any suitable components (e.g., custom or off-the-shelf integrated circuits) and/or by additional circuitry as may serve a particular implementation. For example, the microcontroller of control circuit 1608 may be implemented by an MSP430G2452IRSA 16 microcontroller, commercially available from Texas Instruments, or by an equivalent thereof. The current source circuit IC may be implemented by an LT3092 programmable current source commercially available form Linear Technology, or by an equivalent thereof. The sensor circuit IC may be implemented by an AS-M15SA-R magnetic sensor, commercially available from Murata, or by an equivalent thereof. The switch circuit IC may be implemented by an ADG1419BCPZ single pole double throw analog switch commercially available from Analog Devices, or by an equivalent thereof.

Another feature or enhancement provided by the circuit implementation depicted in FIG. 22 relates to removing, or at least minimizing, some undesirable leading edge transients that are seen in the output stimulus pulses generated by the circuitry of FIG. 21. Specifically, as shown in FIG. 22, an N-MOSFET transistor switch Q1 may be inserted at input terminal IN of current source U3. Transistor switch Q1 may act as a "cascode" stage that helps maintain a more constant voltage across the current source circuit IC as the output current and/or load resistance changes. As shown, the gate terminal (G) of transistor switch Q1 may be driven by battery voltage $V_{BAT}$ which may cause the voltage at source terminal (S) of switch Q1, which is connected to the IN terminal of the current source circuit IC, to be limited to roughly $V_{BAT}-V_{GS}$, where $V_{GS}$ is the threshold voltage across the gate and source terminals of transistor switch Q1.

Use of N-MOSFET transistor switch Q1 as depicted in FIG. 22 may help reduce the transient leading edge of the stimulus pulse because the capacitance looking into Q1 may be much less than is seen when looking into the current source circuit IC because of the Miller effect. In other words, there may be considerable loop gain in the operation of the current source circuit IC to serve the current. The loop gain may directly scale the input capacitance to provide for a much larger leading edge spike on the pulse. Accordingly, a 30 to 40 microsecond transient at the leading edge of the current pulse may be generated as the current source circuit IC recovers current regulation.

Figure 23A:
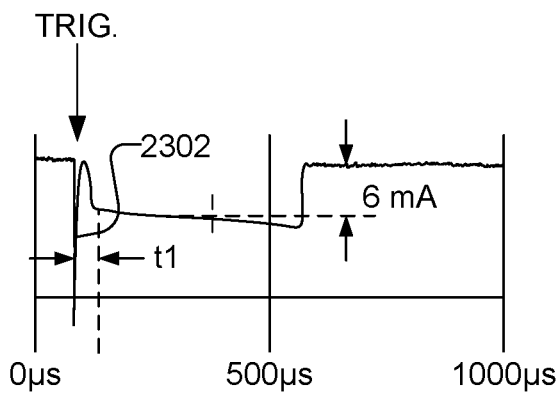
FIGS. 23A and 23B illustrate exemplary timing waveform diagrams that respectively show the operation of the circuit of FIG. 22 before and after the addition of a cascode stage to the circuitry to remove undesirable transients from the leading edge of the stimulus pulse according to principles described herein.

To illustrate, FIG. 23A shows an exemplary timing waveform diagram that includes a leading edge transient. In FIG. 23A, as well as in FIGS. 23B, 23C and 23D, which all show similar timing waveform diagrams, the horizontal axis represents time and the vertical axis represents voltage. In the example of FIGS. 23A through 23D, the voltage represented by the vertical axis may readily be converted to current if a resistive load of 600 ohms is assumed. Currents illustrated in FIGS. 23A through 23D illustrate such currents.

In FIG. 23A, the stimulus pulse begins at a trigger location near the left edge of the waveform, labeled TRIG. As shown, immediately after the trigger point, which should mark the beginning or leading edge of the stimulus pulse, an initial spike 2302 may occur that has a magnitude on the order of twice the amplitude of the stimulus pulse. As illustrated, spike 2302 may shoot down and then back up, and, after a delay of t1 microseconds, may become the leading edge of the stimulus pulse. The delay t1 may be approximately 30-40 microseconds, causing the leading edge of the stimulus pulse to be delayed approximately 30-40 microseconds. However, in certain examples, it may be undesirable for a leading edge to have a delay of this magnitude.

Figure 23B:
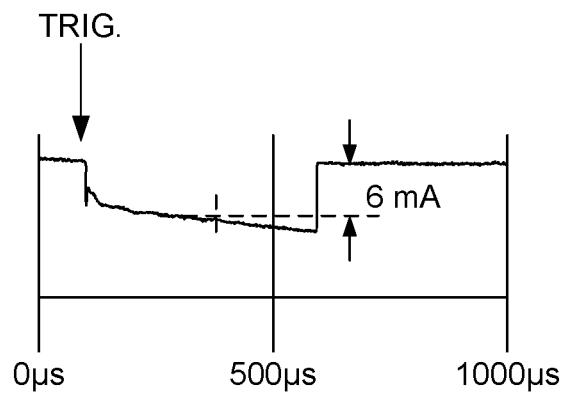

Accordingly, FIG. 23B illustrates the stimulus pulse waveform when the cascode stage (e.g., including transistor switch Q1 as described in relation to FIG. 22) is connected to input terminal IN of current source U3. As shown in FIG. 23B, because the cascode stage may significantly reduce the input capacitance looking into the drain (D) terminal of transistor switch Q1, the leading edge transient may be significantly reduced by the addition of the cascode stage. Specifically, in FIG. 23B, the leading edge transient has all but disappeared, and the delay t1 between the trigger point and the leading edge of the stimulus pulse is negligible.

Figure 23C:
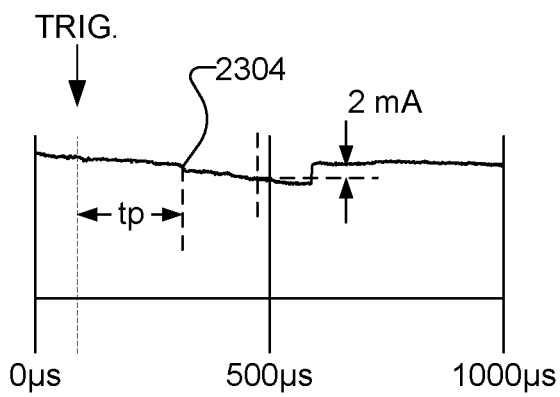
FIGS. 23C and 23D illustrate exemplary timing waveform diagrams that respectively show the operation of the circuit of FIG. 22 before and after the addition of circuitry that addresses a delay when starting a current regulator circuit for low amplitude stimulus pulses according to principles described herein.

Yet another feature or enhancement provided by the circuitry of FIG. 22 involves minimizing a delay that may occur when the programmable current source circuit IC is started up at low pulse amplitudes (e.g., less than about 3 mA). A typical current stimulus output for EA device 100 may be on the order of 15-25 mA. However, when a much smaller amplitude current stimulus is used (e.g., 1.5-3 mA), the control signal defining the smaller amplitude pulse may be significantly less than the one used to define the more typical stimulus amplitudes of 15-25 mA. Such a small control signal may lengthen delay, to, between the trigger point, TRIG, and a leading edge 2304 of the stimulus pulse. FIG. 23C illustrates delay to, which may be on the order of 200 microseconds.

FIG. 23C illustrates a waveform diagram showing this problem. To address the problem, a Schottky diode D5 may be connected (e.g., within the circuit of FIG. 22) from an output port on control circuit 1608 to input port IN of current source U3, as shown. Schottky diode D5 may be implemented by any Schottky diode that may serve a particular implementation. For example, Schottky diode D5 may be implemented by a BAT54XV2DKR diode, commercially available from Fairchild Semiconductor. The BAT54XV2DKR diode may be used to warm-up or "kick start" the current source circuit IC when the pulse amplitude is low in order to minimize delay to before current is regulated at the start of the pulse. Since the cascode stage (i.e., including transistor switch Q1) may keep the drop across the current source circuit IC relatively low, the current source circuit IC may be driven directly from control circuit 1608 at the start of the pulse without significantly changing the pulse characteristics (e.g., amplitude or timing), such that the delay to before current is regulated at the start of the pulse may be reduced.

Figure 23D:
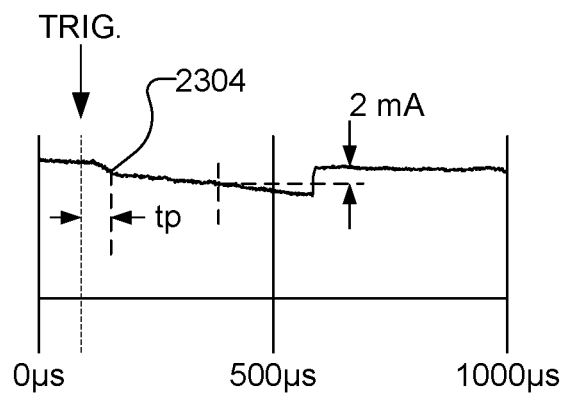

To illustrate, FIG. 23D illustrates the timing waveform diagram achieved using the circuit of FIG. 22 with the diode D5 inserted so as to allow control circuit 1608 to directly drive, or "kick start", the current source circuit IC at the start of the pulse. As seen in FIG. 23D, the delay to realized with the "kick start" has been significantly reduced from what it was without the "kick start" (e.g., as shown in FIG. 23C). For example, the delay to may be reduced from about 200 microseconds to about 40 microseconds, or less. Thus, this "kick start" feature may shorten the undesired delay to by a factor of approximately five or more.

Yet another additional feature provided by the circuitry of FIG. 22 addresses a concern regarding electromagnetic interference ("EMI"). EMI may occur, for example, during electrocautery and/or external defibrillation. Should any of the circuit elements used within EA device 100, such as the switch IC (i.e. the IC labeled U5), have a transient voltage exceeding approximately 0.3 V appear on its pins (which transient voltage could easily occur if EA device is subjected to uncontrolled EMI), then the circuit element could be damaged. Accordingly, to prevent possible EMI damage, the output voltage pulse (i.e. labeled $V_{PULSE}$) may be clamped to ground through the forward bias direction of the diode D3. In contrast, in the circuits shown in FIGS. 19 and 21, there may be two zenor diodes, D2 and D3, connected back to back, to limit the voltage appearing on the $V_{PULSE}$ line to voltages no greater than the zenor diode voltage in either direction. As seen in FIG. 22, diode D2 has been replaced with a short, thereby clamping the voltage that can appear on the output voltage line (i.e., the signal line labeled $V_{PULSE}$) in one polarity direction to no greater than the forward voltage drop across diode D3.

As is evident from the waveforms depicted in FIGS. 23A through 23D, the basic current stimulus waveform may not be a square wave with a "flat top" (or, in the case of a negative current waveform, with a "flat bottom"), as depicted in most simplified waveform diagrams (e.g., such as illustrated in FIG. 4A). Rather, the current stimulus waveforms shown in FIGS. 23A through 23D have what may be referred to in the art as a reverse trapezoidal shape. That is, the current waveforms start at a first value, at the leading edge of the pulse, and gradually ramp to a second, larger, value at the trailing edge of the pulse (i.e., such that the current increases during the pulse). For a negative-going pulse, as is shown in these figures, the ramp slopes downward, but this corresponds to the amplitude of the pulse getting larger.

The reverse trapezoidal pulse shape illustrated in FIGS. 23A through 23D may be desirable and may be implemented by design. For example, the reverse trapezoidal pulse shape may be implemented in order that the current may increase during the pulse to more selectively recruit smaller fiber diameter tissue and nerves, thus potentially activating desired tissue at the target tissue location more effectively.

Figure 24:
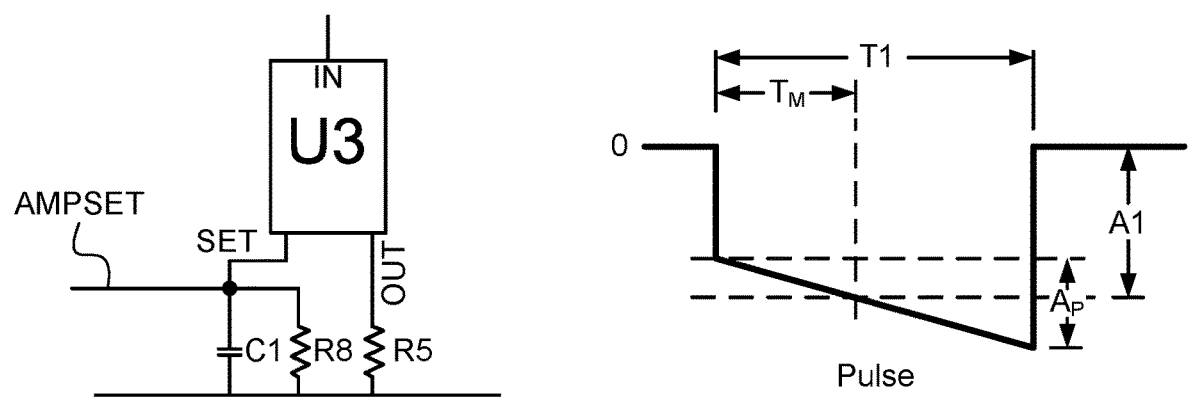
FIG. 24 illustrates an exemplary reverse trapezoidal waveform of the type that may be generated by the pulse generation circuitry of the EA device illustrated in FIG. 1 according to principles described herein.

FIG. 24 illustrates the reverse trapezoidal stimulus pulse shape and an exemplary way of achieving the reverse trapezoidal stimulus pulse shape. Specifically, on the right, FIG. 24 includes a sketch of reverse trapezoidal pulse. The "reverse" is included in the term "reverse trapezoidal pulse" to indicate that the waveform (e.g., the current) may increase during the pulse. In contrast, a conventional voltage regulated pulse may be a "trapezoidal pulse," but may include a current decrease opposite to the increase of the reverse trapezoidal pulse. As shown in FIG. 24, the reverse trapezoidal pulse may have a duration T1, but the magnitude (i.e., amplitude) of the current during the pulse may increase from a first value at the leading edge of the pulse to a second value at the trailing edge of the pulse. As further shown in FIG. 24, the increase in current from the leading edge of the pulse to the trailing edge may have a value $A_P$. The average amplitude of the pulse during the pulse time T1 may have a value A1, which may be measured at a time $T_M$, approximately in the middle of the pulse (i.e., such that $T_M$ is approximately equal to one half of T1).

Also shown in FIG. 24, on the left side, is the circuitry that is used to generate the reverse trapezoidal waveform. This circuitry may be included with the circuitry illustrated in FIG. 22, or with the circuitry in one or more of the other figures described above. The circuitry for generating the reverse trapezoidal waveform may include a capacitor C1 in parallel with a large resistor R8 (e.g., a 270 KΩ resistor), and may be connected to the "SET" terminal of current source U3. The "AMPSET" signal, generated by control circuit 1608 (i.e., microcontroller U2) to set the amplitude A1 of the current stimulus pulse to be generated, may be applied to the "SET" terminal of the current source circuit IC. When enabled by the AMPSET signal, capacitor C1 may start to charge up during the pulse at a rate of approximately 10 μA (e.g., based on the "SET" pin of the current source circuit IC). For example, if C1 is equal to 0.1 microfarads, the rate may be 100 mV/ms, resulting in 50 mV for a pulse having a pulse width T1 of 0.5 ms. Since the pulse current may be approximately equal to $V_{SET}$ divided by R5, the pulse current may increase by 50 mV divided by R5. Thus, if R5 has a value of 22 ohms, this increase in current turns out to be 50 mV ÷ 22 ohms=2.27 mA at the end of the 0.5 ms pulse. This increase may essentially be fixed regardless of the programmed pulse amplitude.

While the circuitry described above may perform the intended function of causing the current stimulus pulse to have a reverse trapezoidal shape in a simple and straightforward manner, it will be understood that there may be other circuits and/or techniques that could similarly be used to achieve the same result in other implementations. Moreover, in some examples, it may be possible to directly control the shape of the $V_{SET}$ signal during the pulse duration in order to create any desired stimulus pulse shape.

As shown in the implementation of EA device 100 shown in FIG. 22, the stimulation circuitry may use a microcontroller IC (i.e., microcontroller U2) to generate all of the operating control signals needed to guide other circuits, including boost converter circuit 1604, to generate the desired stream of stimulation pulses. Among these other circuits are the programmable current source IC (i.e., IC U3), the analog switch IC (i.e., IC U5), and the magnetic sensor IC (i.e., IC U4). As can be seen in FIG. 22, the microcontroller IC may be driven by a clock circuit that includes a crystal oscillator to provide a very stable frequency reference. However, when the stimulus pulses are not being generated (i.e., most of the time given the very low duty cycle of operation less than approximately 0.05), the microcontroller IC may be able to go into a very low power sleep state, thereby conserving power.

In order for the present invention to provide accurate chronotherapeutics (i.e., the delivery of stimulation sessions having very precise stimulation parameters at very precise times), it may be desirable to use a crystal time base. In certain microcontroller IC designs, however, the crystal clock circuit may not provide an accurate time base. Rather, certain microcontroller IC designs may only provide a steady or stable clock signal that can be counted using simple counter circuits. In contrast, a crystal time base may accurately perform all the functions of a sophisticated stop watch, including keeping track of multiple time bases.

A crystal time base may operate all the time in order to provide accurate chronotherapeutics. As such, the crystal time base may roughly double the battery current between therapy sessions, thereby taking the nominal longevity of EA device 100 down roughly from 3 years to 2 years. Unfortunately, reducing the longevity of EA device 100 by a factor of ⅓ may not be a desirable tradeoff for the goal of providing accurate chronotherapeutics. Accordingly, an alternate approach may be desirable to provide an accurate time base without sacrificing the longevity of EA device 100.

To this end, another small IC may be added to the circuitry of EA device 100 that may function as a real time clock ("RTC"). An RTC may be implemented by a very small device (e.g., 3.2×1.5 mm) that may run on only about 360 nanoamps ("nA") of current. Such an RTC may be referred to as a Real Time Clock Module, and may be commercially available from Micro Crystal AG, of Grenchen, Switzerland, as part number RV-4162-C7.

From the above description, it is seen that implantable EA device 100 is provided that uses a digital control signal to duty-cycle limit the instantaneous current drawn from the battery by a boost converter. Various different exemplary functional configurations have been provided for achieving this result, and various exemplary circuit designs or implementations have been presented that may be used to realize the desired configurations.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A method of treating osteoarthritis, comprising:
generating, by an implantable stimulator, stimulation sessions at a duty cycle that is less than 0.05, wherein
the duty cycle is a ratio of T3 to T4,
each stimulation session included in the stimulation sessions has a duration of T3 minutes and occurs at a rate of once every T4 minutes, and
the implantable stimulator comprises a central electrode of a first polarity centrally located on a first surface of a housing of the implantable stimulator and an annular electrode of a second polarity and that is spaced apart from the central electrode; and
applying, by the implantable stimulator, the stimulation sessions by way of the central electrode and the annular electrode to a location within a patient that includes at least one of an acupoint labeled ST35, an acupoint labeled EX-LE-4, or a location on a line that intersects the acupoints labeled ST35 and EX-LE-4.

2. The method of claim 1, wherein the implantable stimulator is powered by a rechargeable battery.

3. The method of claim 2, further comprising receiving, by the implantable stimulator from an external controller, a power signal configured to recharge the rechargeable battery.

4. The method of claim 1, wherein the implantable stimulator is powered by a primary battery.

5. The method of claim 4, wherein the primary battery has an internal impedance greater than 5 ohms.

6. The method of claim 1, wherein the housing of the implantable stimulator is coin-sized and coin-shaped.

7. The method of claim 1, wherein the annular electrode is located on the first surface of the housing.

8. The method of claim 1, wherein the annular electrode comprises a ring electrode located around a perimeter edge of the housing.

9. The method of claim 8, wherein the annular electrode comprises a plurality of electrode segments each having the second polarity and spaced apart from each other in a circumferential pattern around the central electrode.

10. The method of claim 1, wherein T3 is at least 10 minutes and less than 60 minutes, and wherein T4 is at least 1440 minutes.

11. The method of claim 1, wherein:
a lead is attached to the implantable stimulator; and
the applying the stimulation sessions further comprises applying one or more of the stimulation sessions by way of a plurality of electrodes located on the lead.

12. A method of treating osteoarthritis, comprising:
generating, by an implantable stimulator configured to be implanted beneath a skin surface of a patient, stimulation sessions at a duty cycle that is less than 0.05, wherein
the duty cycle is a ratio of T3 to T4, and
each stimulation session included in the stimulation sessions has a duration of T3 minutes and occurs at a rate of once every T4 minutes; and
applying, by the implantable stimulator in accordance with the duty cycle, the stimulation sessions to a location that includes at least one of an acupoint labeled ST35, an acupoint labeled EX-LE-4, or a location on a line that intersects the acupoints labeled ST35 and EX-LE-4.

13. An implantable stimulator, comprising:
a housing;
a central electrode of a first polarity and centrally located on a first surface of the housing;
an annular electrode of a second polarity and that surrounds the central electrode on the first surface of the housing, the annular electrode being spaced apart from the central electrode; and
pulse generation circuitry located within the housing, the pulse generation circuitry configured to
generate stimulation sessions at a duty cycle that is less than 0.05, and
apply the stimulation sessions to a patient by way of the central electrode and the annular electrode a location that includes at least one of an acupoint labeled ST35, an acupoint labeled EX-LE-4, or a location on a line that intersects the acupoints labeled ST35 and EX-LE-4;
wherein
the duty cycle is a ratio of T3 to T4, and
each stimulation session included in the stimulation sessions has a duration of T3 minutes and occurs at a rate of once every T4 minutes.

14. The implantable stimulator of claim 13, further comprising a rechargeable battery within the housing and configured to provide power to the pulse generation circuitry.

15. The implantable stimulator of claim 14, further comprising a receiver circuit within the housing and configured to receive, from an external controller, a power signal configured to recharge the rechargeable battery.

16. The implantable stimulator of claim 13, further comprising a primary battery within the housing and configured to provide power to the pulse generation circuitry.

17. The implantable stimulator of claim 16, wherein the primary battery has an internal impedance greater than 5 ohms.

18. The implantable stimulator of claim 13, wherein the housing of the implantable stimulator is coin-sized and coin-shaped.

19. The implantable stimulator of claim 13, wherein the annular electrode is located on the first surface of the housing.

20. The implantable stimulator of claim 13, wherein the annular electrode comprises a ring electrode located around a perimeter edge of the housing.

* * * * *